US009238680B2

(12) United States Patent
Hua et al.

(10) Patent No.: US 9,238,680 B2
(45) Date of Patent: Jan. 19, 2016

(54) ENGINEERING HEAT-STABLE DISEASE RESISTANCE IN PLANTS

(75) Inventors: Jian Hua, Ithaca, NY (US); Ying Zhu, Hangzhou (CN)

(73) Assignee: Cornell University, Ithaca, NY (US)

( * ) Notice: Subject to any disclaimer, the term of this patent is extended or adjusted under 35 U.S.C. 154(b) by 811 days.

(21) Appl. No.: 13/140,779

(22) PCT Filed: Dec. 21, 2009

(86) PCT No.: PCT/US2009/069082
§ 371 (c)(1),
(2), (4) Date: Aug. 18, 2011

(87) PCT Pub. No.: WO2010/071897
PCT Pub. Date: Jun. 24, 2010

(65) Prior Publication Data
US 2012/0030835 A1    Feb. 2, 2012

Related U.S. Application Data

(60) Provisional application No. 61/139,369, filed on Dec. 19, 2008.

(51) Int. Cl.
*C07K 14/415* (2006.01)
*C12N 15/82* (2006.01)

(52) U.S. Cl.
CPC .......... *C07K 14/415* (2013.01); *C12N 15/8279* (2013.01)

(58) Field of Classification Search
None
See application file for complete search history.

(56) References Cited

U.S. PATENT DOCUMENTS

2005/0076406 A1* 4/2005 Gebhardt et al. ............. 800/279
2005/0193441 A1* 9/2005 Eby .............................. 800/278

OTHER PUBLICATIONS

ENA. *Glycine max* (soybean) R 3 protein. Accession AAO23066.1. 2002.*
Uniprot. Q84ZV8 (Q84ZV8_SOYBN). 2003.*
Halterman et al. The MLA6 coiled-coil, NBS-LRR protein confers AvrMla6-dependent resistance specificity to Blumeria graminis f. sp. hordei in barley and wheat. 2001. 25(3):35-348.*
Yoshimura et al., "Expression of *Xa1*, a Bacterial Blight-Resistance Gene in Rice, is Induced by Bacterial Inoculation," *Proc. Nati. Acad. Sci. USA* 95:1663-1668 (1998).
First Office Action issued in Chinese Patent Application No. 200980157212.8, mailed Nov. 2, 2012 (English Language Translation Provided) (24 pages).
Afzal et al., "Plant Receptor-Like Serine Threonine Kinases: Roles in Signaling and Plant Defense," *MPMI* 21:507-517 (2008).
Jung et al., "The leucine-rich repeat (LRR) protein, CaLRR1, interacts with the hypersensitive induced reaction (HIR) protein, CaHIR1, and suppresses cell death induced by the CaHIR1 protein," *Molecular Plant Pathology* 8:503-514 (2007).
Stange et al., "The N-homologue LRR domain adopts a folding which explains the TMV-Cg-induced HR-like response in sensitive tobacco plants," *Journal of Molecular Graphics and Modeling* 26: 850-860 (2007).
Written Opinion for International Application No. PCT/US2009/069082, completed Aug. 11, 2010.
International Search Report for International Application No. PCT/US/2009/069082, mailed Aug. 13, 2010.
Notification Concerning Transmittal of Copy of International Preliminary Report on Patentability for International Application No. PCT/US2009/069082, mailed Jun. 30, 2011.
Second Office Action issued in Chinese Patent Application No. 200980157212.8, mailed Jul. 8, 2013 (English Language Translation Provided) (14 pages).
Fourth Office Action issued in Chinese Patent Application No. 200980157212.8, mailed Dec. 17, 2014 (English Language Translation Provided) (12 pages).
Third Office Action for Chinese Patent Application No. 200980157212.8, mailed Apr. 1, 2014 (English language translation provided) (20 pages).
Alcazar et al., "The impact of temperature on balancing immune responsiveness and growth in Arabidopsis," Trends Plant Sci 16(12):666-75 (2011).
Burch-Smith et al., "A novel role for the TIR domain in association with pathogen-derived elicitors," PLoS Biol 5(3)e68:0501-14 (2007).
Chisholm et al., "Host-microbe interactions: shaping the evolution of the plant immune response," Cell 124:803-14 (2006).
Clark et al., "Common sequence polymorphisms shaping genetic diversity in Arabidopsis thaliana," Science 317:338-342 (2007).
Dangl et al., "Plant pathogens and integrated defence responses to infection," Nature 411:826-833 (2001).
Dietrich et al., "Arabidopsis mutants simulating disease resistance response," Cell 77:565-577 (1994).
Flor, "Current status of the gene-for-gene concept," Annu. Rev. Phytopathol 9:275-296 (1971).
Hammond-Kosack et al., "Resistance gene-dependent plant defense responses," The Plant Cell 8:1773-1791 (1996).
Hua, "Modulation of plant immunity by light, circadian rhythm, and temperature," Curr Opin Plant Biol 16:406-413 (2013).
Hwang et al., "Evidence for a role of the N terminus and leucine-rich repeat region of the Mi gene product in regulation of localized cell death," The Plant Cell 12:1319-1329 (2000).
Jirage et al., "Arabidopsis thaliana PAD4 encodes a lipase-like gene that is important for salicylic acid signaling," Proc Natl Acad Sci USA 96(23):13583-8 (1999).
Jones et al., "The plant immune system," Nature 444:323-9 (2006).
Lange et al., "Classical nuclear localization signals: definition, function, and interaction with importin alpha," J Biol Chem 282(8):5101-5 (2007).
Lawton et al., "Systemic acquired resistance in Arabidopsis requires salicylic acid but not ethylene," Mol Plant Microbe Interact 8(6):863-870 (1995).
Li et al., "The TIR-NB-LRR gene SNC1 is regulated at the transcript level by multiple factors," Mol Plant Microbe Interact 20(11):1449-56 (2007).

(Continued)

*Primary Examiner* — Steven Bernacki
(74) *Attorney, Agent, or Firm* — Clark & Elbing LLP

(57) ABSTRACT

Disclosed are nucleic acid molecules which encode heat-stable plant resistance polypeptides having NB-LRR structural motifs, where the polypeptide confers heat-stability to a plant defense response. The invention further involves transgenic plants and transformed host cells that express these nucleic acid molecules and exhibit enhanced disease resistance over a wide range of temperatures.

27 Claims, 12 Drawing Sheets

(56) References Cited

OTHER PUBLICATIONS

Lukowitz et al., "Positional cloning in Arabidopsis. Why it feels good to have a genome initiative working for you," Plant Physiol 123:795-805 (2000).

Martin et al., "Understanding the functions of plant disease resistance proteins," Annu. Rev. Plant Biol. 54:23-61 (2003).

Merkle, "Nucleo-cytoplasmic transport of proteins and RNA in plants," Plant Cell Rep 30:153-176 (2011).

Nurnberger et al., "Innate immunity in plants and animals: striking similarities and obvious differences," Immunol Rev 198:249-266 (2004).

Palma et al., "An importin alpha homolog, MOS6, plays an important role in plant innate immunity," Curr Biol 15:1129-1135 (2005).

Rairdan et al., "Distinct domains in the ARC region of the potato resistance protein Rx mediate LRR binding and inhibition of activation," The Plant Cell 18:2082-2093 (2006).

Rathjen et al., "Early signal transduction events in specific plant disease resistance," Curr Opin Plant Biol 6:300-306 (2003).

Shen et al., "Nuclear activity of MLA immune receptors links isolate-specific and basal disease-resistance responses," Science 315:1098-1103 (2007).

Someya et al., "Pattern of N gene-mediated systemic hypersensitive response and turnover of viral replicase protein in tobacco," Arch Virol 149:2105-2113 (2004).

Takken et al., "Resistance proteins: molecular switches of plant defence," Curr Opin Plant Biol 9:383-90 (2006).

Takken et al., "How to build a pathogen detector: structural basis of NB-LRR function," Curr Opin Plant Biol 15:375-384 (2012).

Tzfira et al., "pSAT vectors: a modular series of plasmids for autofluorescent protein tagging and expression of multiple genes in plants," Plant Mol Biol 57:503-516 (2005).

Uknes et al., "Acquired resistance in Arabidopsis," The Plant Cell 4:645-656 (1992).

Wen et al., "Identification of a signal for rapid export of proteins from the nucleus," Cell 82:463-473 (1995).

Whitham et al., "The product of the tobacco mosaic virus resistance gene N: similarity to toll and the interleukin-1 receptor," Cell 78:1101-1115 (1994).

Xiao et al., "The Arabidopsis Gene RPW8.1 and RPW8.2 confer induced resistance to powdery mildew diseases in tobacco," Mol Plant Microbe Interact 16(4):289-294 (2003).

Xu et al., "The nuclear pore comes to the fore," Trends in Plant Science 13(1):20-27 (2008).

Yang et al., "A haplotype-specific resistance gene regulated by BONZAI1 mediates temperature-dependent growth control in Arabidopsis," The Plant Cell 16:1060-1071 (2004).

Yang et al., "The C2 domain protein BAP1 negatively regulates defense responses in Arabidopsis," Plant J 48:238-48 (2006).

Yang et al., "The Arabidopsis BAP1 and BAP2 genes are general inhibitors of programmed cell death," Plant Physiol 145:135-46 (2007).

Yoshioka et al., "Environmentally sensitive, SA-dependent defense responses in the cpr22 mutant of Arabidopsis," Plant J 26(4):447-59 (2001).

Yue et al., "Tracing the origin and evolutionary history of plant nucleotide-binding site-leucinerich repeat (NBS-LRR) genes," New Phytologist 193:1049-1063 (2012).

Zhang et al., "A gain-of-function mutation in a plant disease resistance gene leads to constitutive activation of downstream signal transduction pathways in suppressor of npr1-1, constitutive 1," The Plant Cell 15:2636-2646 (2003).

Zhang et al., "A putative nucleoporin 96 is required for both basal defense and constitutive resistance responses mediated by suppressor of npr1-1, constitutive 1," The Plant Cell 17:1306-1316 (2005).

* cited by examiner

Figure 7

```
MEIASSSGSRRYDVFPSFRGEDVRDSFLSHLLKELRGKAITFIDDEIERSRSIGPELLSAIKESRIAIVI    TIR
FSKNYASSTWCLNELVEIHKCYTNLNQMVIPIFFHVDASEVKKQTGEFGKVFEETCKAKSEDEKQSWKQA
LAAVAVMAGYDLRKWPSEAAMIEELAEDVLRKTMTPSDDPGDLVGIENHIEAIKSVLCLESKEARIMVGI
WGQSGIGKSTIGRALYSKLSIQFHHRAFITYKSTSGSDVSGMKLRWEKELLSEILGQKDIKIEHFGVVEQ    NB-ARC
RLKQQKVLILLDDVDSLEFLKTLVGKAEWPGSGSRIIVITQDRQLLKAHEIDLIYEVEFPSEHLALTMLC
RSAFGKDSPPDDFKELAFEVAKLAGNLPI$\underline{\text{G}}$LSVLGSSLKGRTKEWNMEMMPRLRNGLNGDIMKTLRVSYD
RLHQKDQDMFLYIACLFNGFBVSYVKDLLKDNVGFTMLTEKSLIRITPDGYIEMHNLLEKLGREIDRAKS
KGNPGKRRFLTNFEDIHEVVTEKTGTETLLGIRLPFEEYFSTRPLLIDKESFKGMRNLQYI$\underline{\text{E}}$IGYYGDLP
QSLVYLPLKLRLLDWDDCPLKSLPSTFKAEYLVNLIMKYSKLEKLWEGT<u>LPLGSLKEMNLRYSNNLKEIP</u>
<u>DLSLAINLEELDLVGCKSLVTLPSSIQNATKI,IYLDMSDCKKLESPPTDLNLESLEYLNLTGCPNLRNFP</u>
<u>AIKMGCSDVDFPBGRNEIVVEDCFWNKNLPAGLDYLDCLTRCMPCEFRPEQLAFLNVRGYKHEKLWEGIQ</u>
<u>SLGSLEGMDLSESENLTEIPDLSKATKLESLILNNCKSLVTLPSTIGNLHRLVRLEMKECTGLEVLPTDV</u>    LRR
<u>NLSSLETLDLSGCSSLRSFPLISTNIVWLYLENTAIEEIPSTIGNLHRLVRLEMKKCTGLEVLPTDVNLS</u>
<u>SLETLDLSGCSSLRSFPLISESIKWLYLENTAIEEIPDLSKATNLKNLKLNNCKSLVTLPTTIGNLQKLV</u>
<u>SFEMKECTGLEVLPIDVNLSSLMILDLSGCSSLRTFPLISTNIVWLYLENTAIEEIPSTIGNLHRLVKLE</u>
<u>MKECTGLEVLPTDVNLSSLMILDLSGCSSLRTFPLISTRIECLYLQNTAIEEVPCCIEDFTRLTVLMMYC</u>
<u>CQRLKTISFNIFRLTRLELADFTDCRGVIKALSDATVVATMEDHVSCVPLSENIEYIWDKLYHLPSKLNF</u>
NDVEFKFCCSNRIKECGVRLMYVSQEENNQQTTRSEKRMRMTSGTSEEDINLPYGLIVADTGLAALNMEL
SLGQGEPSSSTSLEGEALCVDYMITEEQDKGIPILFPVSGN    (SEQ ID NO.: 1)
```

Figure 8A

| | | | | |
|---|---|---|---|---|
| NP_193422.1 | NP_193173.1 | NP_199333.1 | ABG01419.1 | ABG00998.1 |
| NP_851172.1 | CAB10461.1 | NP_177427.2 | ABF74109.1 | ABG01094.1 |
| BAB08679.1 | NP_199264.1 | NP_193429.1 | ABF74098.1 | ABG00988.1 |
| NP_199976.2 | ABS82020.1 | NP_197290.1 | ABG01383.1 | AAD25848.3 |
| AAN86124.1 | ABS82021.1 | NP_199319.1 | ABF74119.1 | NP_193421.2 |
| NP_193428.2 | AAM18462.1 | BAB11221.1 | ABF74139.1 | NP_001045334.1 |
| NP_849398.1 | NP_199725.1 | NP_199300.1 | ABF74087.1 | CAB10464.1 |
| NP_197298.1 | NP_197338.1 | NP_199318.2 | ABF74125.1 | NP_683486.1 |
| CAB46048.1 | NP_196686.1 | NP_190049.1 | ABF74136.1 | ABG01208.1 |
| D71437 | NP_199463.1 | NP_190725.1 | ABF74106.1 | ABG01201.1 |
| NP_198970.1 | NP_193420.2 | NP_195338.1 | ABF74111.1 | ABG01205.1 |
| NP_179279.1 | CAB80962.1 | NP_850655.1 | ABG01395.1 | ABG01197.1 |
| NP_200620.1 | AAF24575.1 | NP_851133.1 | ABG01410.1 | ABG01248.1 |
| NP_197337.1 | NP_176047.1 | NP_199688.1 | ABF74124.1 | ABG01209.1 |
| NP_197661.1 | BAB10820.1 | NP_195337.1 | ABF74086.1 | ABF73632.1 |
| NP_176571.1 | AAM53313.1 | AAO45748.1 | ABF74133.1 | ABF73595.1 |
| NP_198990.3 | NP_199464.2 | NP_198509.2 | ABG01439.1 | ABF73596.1 |
| AAG51270.1 | AAG60098.1 | NP_001119319.1 | ABG01422.1 | ABF73641.1 |
| AAG60157.1 | DAE98880.1 | BAB11635.1 | ABF74089.1 | BAF01484.1 |
| NP_001117396.1 | NP_193424.2 | NP_193688.1 | ABF74116.1 | ABF73605.1 |
| NP_174439.2 | NP_176590.2 | NP_179297.2 | ABG01375.1 | ABF73590.1 |
| NP_198907.1 | NP_197336.1 | BAD38678.1 | ABF74110.1 | ABF73604.1 |
| NP_199438.1 | AAM97118.1 | AAF18599.1 | ABG01418.1 | ABF73616.1 |
| AAS01763.1 | AAC72978.1 | NP_199339.2 | ABF74093.1 | ABF73617.1 |
| AAL36373.1 | NP_198989.2 | NP_199336.1 | ABF74140.1 | ABF73623.1 |
| B71437 | BAE99086.1 | NP_199334.1 | ABG01370.1 | ABF73639.1 |
| NP_198969.1 | NP_192939.2 | BAC41834.1 | ABF74092.1 | ABF73603.1 |
| CAB10466.1 | NP_001118968.1 | NP_001078715.1 | ABF74123.1 | ABF73599.1 |
| AAL91293.1 | BAE98800.1 | AAO45749.1 | ABF74129.1 | ABF73619.1 |
| AAL07075.1 | NP_176043.1 | AAD55631.1 | ABF74112.1 | ABF73649.1 |
| NP_199439.2 | AAC72977.1 | NP_190724.1 | ABF74117.1 | ABF74258.1 |
| BAB11082.1 | CAB88530.1 | BAB11222.1 | NP_192681.1 | ABF73612.1 |
| NP_192585.1 | AAG09110.1 | BAE99034.1 | ABG01399.1 | ABF73654.1 |
| BAA97409.1 | NP_190034.2 | NP_197291.2 | ABG01384.1 | ABF73591.1 |
| NP_193425.1 | NP_176044.1 | AAG13419.1 | ABG01426.1 | ABF73660.1 |
| BAA97354.1 | AAFC8790.1 | NP_174038.1 | ABF74122.1 | ABF74233.1 |
| BAC41800.2 | NP_193427.1 | NP_174037.3 | ABG01368.1 | ABF73673.1 |
| BAB10815.1 | NP_001078237.1 | NP_179298.2 | ABG01430.1 | ABG01607.1 |
| CAB43052.1 | BAD94052.1 | AAF18600.1 | ABF74095.1 | ABF73602.1 |
| NP_199457.1 | CAB72469.1 | NP_974894.1 | NP_198826.1 | ABF73588.1 |
| NP_198650.1 | NP_190026.1 | AAF79477.1 | ABG01412.1 | ABF73634.1 |
| NP_001077769.1 | AAC72979.1 | NP_173203.1 | ABG01420.1 | ABF73597.1 |
| AAG52417.1 | AAM13214.1 | AAG13418.1 | BAB09118.1 | ABG01548.1 |
| NP_198651.1 | NP_192938.1 | CAA16929.1 | ABG01407.1 | ABF73621.1 |
| NP_199459.2 | AAR92462.1 | NP_564971.1 | AAD55633.1 | ABF73611.1 |
| NP_187072.1 | BAC42557.1 | NP_177429.2 | BAF01370.1 | ABF74263.1 |
| NP_176561.2 | ABB00837.1 | NP_193687.2 | ABG00946.1 | ABG01574.1 |
| NP_192855.1 | ABB00835.1 | ABG01388.1 | ABG00949.1 | ABF74292.1 |
| AAM20596.1 | ABB00834.1 | ABG01367.1 | ABG01024.1 | ABG01661.1 |
| BAE98908.1 | ABB00838.1 | ABG01389.1 | ABG01022.1 | ABG01561.1 |
| NP_001077768.1 | NP_193685.3 | ABG01364.1 | ABG01034.1 | ABF73633.1 |
| NP_176560.1 | NP_199338.1 | ABG01435.1 | ABG01044.1 | ABG01575.1 |
| BAC43641.2 | ABB00836.1 | ABG01423.1 | ABG01119.1 | ABG01581.1 |
| NP_176572.1 | CAB53784.1 | ABG01408.1 | ABG01036.1 | ABG01537.1 |
| BAE98749.1 | CAA16927.2 | ABG01361.1 | ABG00991.1 | ABF73626.1 |
| NP_198701.1 | CAB53785.1 | ABG01393.1 | ABG01043.1 | ABF74221.1 |
| NP_189178.1 | NP_176078.1 | ABG01372.1 | ABG01041.1 | ABF73659.1 |
| NP_176760.2 | BAB01321.1 | ABG01366.1 | ABG01039.1 | ABG01583.1 |
| NP_179024.1 | ABB00841.1 | ABG01369.1 | ABG01058.1 | ABG01593.1 |
| AAM15274.1 | CAA16928.1 | ABG01362.1 | ABG01076.1 | ABG01555.1 |
| BAB09567.1 | NP_193686.2 | ABF74126.1 | ABG01050.1 | ABG01536.1 |
| NP_197270.1 | BAF01192.1 | ABF74127.1 | ABG00983.1 | ABG01535.1 |
| BAB10522.1 | BAB11393.1 | ABG01434.1 | ABG01006.1 | ABF74295.1 |

Figure 8B

| | | |
|---|---|---|
| ABF74248.1 | ABF73601.1 | ABG00690.1 |
| ABF74282.1 | ABF73606.1 | ABG00724.1 |
| ABF74224.1 | ABG01658.1 | ABG00691.1 |
| ABF74241.1 | ABF73671.1 | ABG00719.1 |
| ABF74235.1 | ABG01586.1 | BAB10245.1 |
| ABF73625.1 | ABF73655.1 | ABG00697.1 |
| ABG01599.1 | ABG01589.1 | ABG01139.1 |
| ABF73598.1 | ABG01579.1 | ABG01137.1 |
| ABG01585.1 | ABG01559.1 | ABG00705.1 |
| ABF73618.1 | ABB00875.1 | ABG01123.1 |
| ABF73640.1 | NP_001067491.1 | ABG00731.1 |
| ABF73608.1 | ABB00889.1 | ABG00703.1 |
| ABF73678.1 | ABF73725.1 | ABG01141.1 |
| ABF73607.1 | ABF73684.1 | ABG00708.1 |
| ABF74281.1 | ABF73729.1 | ABG01160.1 |
| ABF74220.1 | ABF73682.1 | ABG01134.1 |
| ABF74232.1 | ABF73721.1 | NP_001068347.1 |
| ABG01619.1 | ABF73732.1 | ABB00893.1 |
| ABG01628.1 | ABF73686.1 | ABB00891.1 |
| ABF74226.1 | ABF73755.1 | ABG01131.1 |
| ABF74231.1 | ABF73722.1 | ABG00732.1 |
| ABG01538.1 | ABF73679.1 | ABG01161.1 |
| ABG01533.1 | ABF73694.1 | ABG00707.1 |
| ABG01551.1 | ABF73670.1 | NP_001059355.1 |
| ABG01648.1 | ABF73681.1 | ABG00709.1 |
| ABG01639.1 | ABF73698.1 | ABG00701.1 |
| ABG01562.1 | ABF73720.1 | NP_001067497.1 |
| ABG01600.1 | ABF73742.1 | ABG00699.1 |
| ABG01677.1 | ABF73718.1 | NP_001047326.1 |
| ABG01553.1 | ABF73680.1 | NP_001058185.1 |
| ABG01541.1 | ABF73719.1 | NP_001055149.1 |
| ABG01554.1 | ABF73449.1 | NP_001067488.1 |
| ABF73609.1 | ABF73439.1 | NP_193640.1 |
| ABG01531.1 | ABF74253.1 | NP_001068349.1 |
| ABF74246.1 | ABF74294.1 | ABG00747.1 |
| ABG01540.1 | ABF73703.1 | O50052 |
| ABG01591.1 | ABF73422.1 | BAD94108.1 |
| ABG01556.1 | ABF73429.1 | ABG00742.1 |
| ABG01569.1 | ABF73436.1 | CAO43337.1 |
| ABF74222.1 | ABF73493.1 | NP_001062397.1 |
| ABG01622.1 | ABF73466.1 | NP_195056.2 |
| ABF73664.1 | ABF73424.1 | Q9SZA7 |
| ABF73589.1 | ABF73434.1 | CAB38788.1 |
| ABF73675.1 | ABF73459.1 | ACD76094.1 |
| ABG01567.1 | ABF73423.1 | ABG00782.1 |
| ABG01594.1 | ABF73425.1 | ABG00771.1 |
| ABF73635.1 | ABF73430.1 | ABG00813.1 |
| ABG01601.1 | ABF73467.1 | ABG00761.1 |
| ABF73657.1 | ABF73485.1 | ABG00748.1 |
| ABG01557.1 | ABF73490.1 | ABG00765.1 |
| ABG01552.1 | ABB00900.1 | ABG00785.1 |
| ABF74227.1 | NP_001043262.1 | ABG00770.1 |
| ABF73594.1 | NP_199337.2 | ABG00812.1 |
| ABG01588.1 | NP_001062892.1 | ABG00757.1 |
| ABF74287.1 | ABG01153.1 | ABG00753.1 |
| ABF73593.1 | ABG01121.1 | CAO70216.1 |
| ABG01532.1 | EAZ08636.1 | ABG00803.1 |
| ABG01584.1 | ABG01191.1 | ABG00804.1 |
| ABF74291.1 | ABG01188.1 | ABG00762.1 |
| ABG01590.1 | NP_001042644.1 | |
| ABG01543.1 | ABG00706.1 | |
| ABF73638.1 | ABG00698.1 | |
| ABG01587.1 | ABG00693.1 | |

Figure 9A

| Vitis vinifera | CAO44568.1 | CAO16300.1 | CAN64645.1 | ABF81459.1 |
| (wine grape) | CAO16426.1 | CAO16423.1 | CAN63598.1 | ABF81416.1 |
| CAO24746.1 | CAO62662.1 | CAO49900.1 | CAO49606.1 | ABB82027.1 |
| CAO64653.1 | CAO43693.1 | CAO49932.1 | CAO16398.1 | ABF81433.1 |
| CAO16282.1 | CAO16291.1 | CAO49622.1 | CAN68234.1 | ABF81409.1 |
| CAO16318.1 | CAO15447.1 | CAN78790.1 | CAO16330.1 | ABF81410.1 |
| CAN68293.1 | CAO49577.1 | CAO44535.1 | CAO49584.1 | ABF81409.1 |
| CAN84090.1 | CAN69843.1 | CAN81612.1 | CAO16390.1 | ABF81410.1 |
| CAO49904.1 | CAO50047.1 | CAO49953.1 | CAO16334.1 | ABF81409.1 |
| CAO49944.1 | CAO49573.1 | CAO42751.1 | CAO23281.1 | ABF81410.1 |
| CAN83385.1 | CAO16055.1 | CAO50043.1 | CAO16319.1 | ABF81409.1 |
| CAN76615.1 | CAO71533.1 | CAN69078.1 | CAO44577.1 | ABF81410.1 |
| CAO16283.1 | CAO49941.1 | CAO49933.1 | CAN69856.1 | ABB82031.1 |
| CAN71924.1 | CAO15210.1 | CAO40985.1 | CAO49427.1 | ABB82024.1 |
| CAO49942.1 | CAO16288.1 | CAO15207.1 | CAN62507.1 | ABB82028.1 |
| CAO49905.1 | CAO15450.1 | CAO62388.1 | CAN82453.1 | ABE99702.1 |
| CAO16420.1 | CAO71531.1 | CAO49600.1 | CAN78783.1 | ABB82029.1 |
| CAO65792.1 | CAN61526.1 | CAO16388.1 | CAO15448.1 | ABF81419.1 |
| CAO16320.1 | CAO64669.1 | CAO49943.1 | CAN79645.1 | ABF81418.1 |
| CAO49627.1 | CAN63551.1 | CAN68384.1 | CAO16418.1 | ABF81429.1 |
| CAN72303.1 | CAO50049.1 | CAO49792.1 | AAQ15191.1 | ABB82026.1 |
| CAO16286.1 | CAO43123.1 | CAN66808.1 | CAO49611.1 | ABF81471.1 |
| CAO49902.1 | CAO43491.1 | CAO24775.1 | CAO44569.1 | ABF81452.1 |
| CAO16284.1 | CAO70119.1 | CAO16896.1 | CAO66485.1 | ABB82025.1 |
| CAN64759.1 | CAO62661.1 | CAO16397.1 | CAO44573.1 | ABF81440.1 |
| CAN77679.1 | CAO16324.1 | CAO49935.1 | CAO44572.1 | ABB82030.1 |
| CAO16326.1 | CAO49576.1 | CAN75617.1 | CAN64358.1 | ABF81412.1 |
| CAO16306.1 | CAO71529.1 | CAN72925.1 | CAO61278.1 | ABF81465.1 |
| CAO43131.1 | CAO67899.1 | CAN62576.1 | CAN63745.1 | ABF81432.1 |
| CAO49620.1 | CAO70121.1 | CAO16890.1 | CAO50045.1 | ABF81408.1 |
| CAO49901.1 | CAO71538.1 | CAO16295.1 | CAO49575.1 | |
| CAO16416.1 | CAO71537.1 | CAN66451.1 | CAO14504.1 | Solanum |
| CAO50050.1 | CAO16413.1 | CAN61853.1 | CAN76072.1 | tuberosum |
| CAO16321.1 | CAO44544.1 | CAO71540.1 | | (potatoes) |
| CAO16287.1 | CAO16352.1 | CAN74711.1 | Populus | AAP44393.1 |
| CAN78931.1 | CAO44555.1 | CAO49903.1 | trichocarpa | AAP44392.1 |
| CAO16405.1 | CAN70507.1 | CAN81250.1 | (black | AAP44394.1 |
| CAO16303.1 | CAN61627.1 | CAO16408.1 | cottonwood, | AAP44390.1 |
| CAN67940.1 | CAO49580.1 | CAO49595.1 | ...) | AAP44391.1 |
| CAN82909.1 | CAO16253.1 | CAN75767.1 | ABF81417.1 | CAA08798.1 |
| CAN68265.1 | CAN73963.1 | CAO67895.1 | ABF81413.1 | |
| CAO44592.1 | CAN74723.1 | CAO16393.1 | ABF81439.1 | Cucumis melo |
| CAO64662.1 | CAN61773.1 | CAO44531.1 | ABF81428.1 | (Oriental |
| CAO44537.1 | CAO49948.1 | CAO44596.1 | ABF81437.1 | melon) |
| CAO16335.1 | CAN77694.1 | CAN73697.1 | ABF81434.1 | AAU04762.1 |
| CAO43490.1 | CAN75296.1 | CAO24741.1 | ABF81431.1 | AAU04761.1 |
| CAO49934.1 | CAO16391.1 | CAO49582.1 | ABF81431.1 | AAU04763.1 |
| CAO16292.1 | CAN68630.1 | CAO24737.1 | ABF81431.1 | ABB91439.1 |
| CAO15446.1 | CAN67859.1 | CAN72675.1 | ABF81454.1 | AAU04760.1 |
| CAO64667.1 | CAN66453.1 | CAC15213.1 | ABF81431.1 | AAO45748.1 |
| CAO62387.1 | CAC44552.1 | CAO24780.1 | ABF81454.1 | ABR67409.1 |
| CAN68108.1 | CAN82897.1 | CAO16417.1 | ABF81414.1 | AAU04759.1 |
| CAO64659.1 | CAN82538.1 | CAO16900.1 | ABF81427.1 | AAO45749.1 |
| CAO16327.1 | CAO16400.1 | CAO24744.1 | ABF81441.1 | AAU04764.1 |
| CAO16289.1 | CAO16323.1 | CAO64668.1 | ABF81445.1 | AAU04758.1 |
| CAO49940.1 | CAO24785.1 | CAN68030.1 | ABF81441.1 | |
| CAO16427.1 | CAN78885.1 | CAO16389.1 | ABF81445.1 | Medicago |
| CAO71542.1 | CAO24777.1 | CAO17016.1 | ABF81441.1 | sativa |
| CAN75658.1 | CAO16421.1 | CAO24745.1 | ABF81445.1 | (alfalfa, ...) |
| CAO44566.1 | CAO40986.1 | CAO69467.1 | ABF81438.1 | ACF19651.1 |
| CAN78476.1 | CAO17013.1 | CAO24742.1 | ABF81430.1 | |
| CAO44571.1 | CAN68969.1 | CAO24738.1 | ABG37662.1 | |
| CAN73064.1 | CAN83953.1 | CAO16205.1 | ABF81423.1 | |

Figure 9B

| | | | | |
|---|---|---|---|---|
| Populus balsamifera (balsam poplar, ...) ABE99701.1 | ABN05946.1 ABD33309.1 ABD33387.2 ABD28703.1 ABN09183.1 ABN09142.1 ABN08493.1 | Helianthus annuus AAN73007.1 AAL07535.1 AAN73009.1 | (Populus tomentosa x P. bolleana) x P. tomentosa var. truncata ABC55465.1 ABC55466.1 | BAF07248.1 BAD87306.1 EAZ21756.1 BAD38047.1 NP_001062892.1 BAF24806.1 NP_001062892.1 BAF24806.1 EAZ44276.1 |
| Phaseolus vulgaris (French bean, ...) ABH07384.1 ABA00702.1 | Nicotiana tabacum (tobacco, ...) AAT37497.1 BAF95889.1 | Linum usitatissimum AAK28809.1 AAK28812.1 AAK28806.1 AAK28803.1 | Pinus taeda [conifers] AAM28909.1 AAM28911.1 | NP_001042644.1 BAB03441.1 BAF04558.1 EAZ11314.1 |
| Glycine max (soybeans) AAO23067.1 AAO23066.1 AAO23077.1 AAO23075.1 AAO23069.1 AAO92748.1 AAO23074.1 AAO23076.1 AAL56987.1 AAG48132.1 AAG09951.1 AAG09953.1 AAN63807.1 AAL57179.1 AAP74724.1 AAP74723.1 AAP74722.1 AAG09952.1 AAM90028.1 AAG01048.1 AAM90026.1 AAM90025.1 AAM90024.1 AAM90027.1 AAM90029.1 AAM90030.1 AAM90031.1 CAA06201.1 AAG48133.1 AAM90014.1 AAM90010.1 AAM90013.1 AAM90012.1 AAM90008.1 AAM90009.1 AAM90022.1 AAM90011.1 AAM90023.1 AAM90017.1 AAM90018.1 AAM90021.1 AAM90020.1 AAM90019.1 | BAF95888.1 ABO21407.1 BAD12594.1 BAD12595.1 AAG43546.1 Malus baccata (shan jing zi) AAQ93075.1 AAQ93074.1 AAQ93076.1 Populus deltoides CAC95124.1 Nicotiana glutinosa Q40392 AAA50763.1 Q40392 AAA50763.1 Q40392 AAA50763.1 Q40392 AAA50763.1 Solanum lycopersicum (tomato) AAR21295.1 Solanum tuberosum subsp. andigena CAC82811.1 CAC82812.1 Lens culinaris CAD56833.1 Arabidopsis lyrata (lyrate rockcress) ABB00841.1 ABF74395.1 ABF74396.1 ABF74397.1 ABB00900.1 | AAK28810.1 AAK28811.1 AAK28805.1 AAK28808.1 AAK28804.1 CAC35326.1 CAC35339.1 CAC35321.1 CAC35337.1 CAC35329.1 CAC35338.1 CAC35327.1 CAC35333.1 CAC35330.1 CAC35325.1 CAC35336.1 CAC35325.1 CAC35336.1 CAC35325.1 CAC35336.1 CAC35325.1 CAC35332.1 CAC35328.1 CAC35331.1 CAC35323.1 AAB47618.1 AAD25974.1 AAD25976.1 AAD25971.1 AAD25967.1 AAD25970.1 AAD25967.1 AAD25970.1 AAD25967.1 AAD25970.1 AAD25967.1 AAD25970.1 AAD25967.1 AAD25970.1 AAD25965.1 AAD25972.1 AAD25966.1 AAD25969.1 AAD25968.1 AAD25973.1 AAA91022.1 AAA91021.1 | AAM28912.1 AAM28915.1 AAM28917.1 (Populus tomentosa x P. bolleana) x P. tomentosa ABM55687.1 Solanum demissum AAW28561.2 ABI34382.1 ABI34381.1 Oryza sativa Indica Group (Indian rice) EAY77148.1 EAY84492.1 EAZ08637.1 EAY73380.1 EAY77149.1 EAZ06275.1 EAZ08636.1 EAZ03476.1 EAY73511.1 EAY80338.1 EAY80341.1 CAH67345.1 EAY94648.1 CAH67345.1 EAY94648.1 CAH67345.1 EAY94648.1 CAH67345.1 EAY94648.1 EAY80353.1 Oryza sativa Japonica Group (Japanese rice) EAZ14770.1 NP_001045334.1 BAF07248.1 NP_001045334.1 BAF07248.1 NP_001045334.1 | NP_001042644.1 BAB03441.1 BAF04558.1 EAZ11314.1 NP_001042644.1 BAB03441.1 BAF04558.1 EAZ11314.1 NP_001042644.1 BAB03441.1 BAF04558.1 EAZ11314.1 NP_001042644.1 BAB03441.1 BAF04558.1 EAZ11314.1 NP_001042644.1 BAB03441.1 BAF04558.1 EAZ11314.1 EAZ14771.1 EAZ42101.1 EAZ44275.1 BAD23605.1 BAD23621.1 EAZ44283.1 BAD23621.1 EAZ44283.1 BAC84623.1 BAD31615.1 BAC84623.1 BAD31615.1 BAC84623.1 BAD31615.1 BAC84623.1 BAD31615.1 BAC84623.1 BAD31615.1 NP_001059355.1 BAF21269.1 NP_001059355.1 BAF21269.1 NP_001059355.1 BAF21269.1 NP_001059355.1 BAF21269.1 NP_001059355.1 BAF21269.1 NP_001059355.1 BAF21269.1 |
| Medicago truncatula ACF19650.1 ABD28507.1 | | | | |

Figure 9C

```
EAZ39387.1        BAF27860.1
BAD37434.1        EAZ17813.1
NP_001067491.1    NP_001067497.1
ABA92120.1        BAF27860.1
BAF27854.1        EAZ17813.1
EAZ17800.1        NP_001067497.1
NP_001067491.1    BAF27860.1
ABA92120.1        EAZ17813.1
BAF27854.1        NP_001067497.1
EAZ17800.1        BAF27860.1
NP_001067491.1    EAZ17813.1
ABA92120.1        NP_001067497.1
BAF27854.1        BAF27860.1
EAZ17800.1        EAZ17813.1
NP_001067491.1    NP_001067497.1
ABA92120.1        BAF27860.1
BAF27854.1        EAZ17813.1
EAZ17800.1        ABA92135.1
NP_001067491.1    NP_001047326.1
ABA92120.1        BAD21628.1
BAF27854.1        BAF09240.1
EAZ17800.1        NP_001047326.1
NP_001067491.1    BAD21628.1
ABA92120.1        BAF09240.1
BAF27854.1        NP_001047326.1
EAZ17800.1        BAD21628.1
NP_001058185.1    BAF09240.1
BAF20099.1        NP_001047326.1
EAZ37801.1        BAD21628.1
NP_001058185.1    BAF09240.1
BAF20099.1        NP_001047326.1
EAZ37801.1        BAD21628.1
NP_001058185.1    BAF09240.1
BAF20099.1
EAZ37801.1        Picea
NP_001058185.1    sitchensis
BAF20099.1        [conifers]
EAZ37801.1        ABK24822.1
NP_001058185.1
BAF20099.1        Hordeum
EAZ37801.1        vulgare
NP_001067488.1    (barley)
ABA92038.1        CAD45029.1
BAF27851.1
NP_001067488.1
ABA92038.1
BAF27851.1
NP_001067488.1
ABA92038.1
BAF27851.1
NP_001067488.1
ABA92038.1
BAF27851.1
CAE02491.1
CAE01665.2
CAE02491.1
CAE01665.2
CAE02491.1
CAE01665.2
CAE02491.1
CAE01665.2
EAZ31189.1
NP_001067497.1
```

Figure 10

| Species | R Mutation |
|---|---|
| Arabidopsis thaliana | N689D or E801K I803D |
| Populus trichocarpa (black cottonwood) | S630K I632D |
| Solanum tuberosum (potatoes) | V655D |
|  | Q1203K |
| Cucumis melo (Oriental melon) | V675D |
| Medicago sativa (alfalfa) | I703D |
| Populus balsamifera (balsam poplar) | M689D |
| Phaseolus vulgaris (French bean) | S653K V655D |
| Glycine max (soybeans) | E638K S640D |
| Medicago truncatula | V678D |
|  | E505K V507D |
| Nicotiana tabacum (tobacco) | E646K N648D |
| Nicotiana glutinosa | Y646K N648D |
| Solanum lycopersicum (tomato) | Y682K N684D |
|  | F243K F245D |
| Solanum tuberosum subsp. andigena (potato) | Y655K G657D |
| Lens culinaris (lentil) | S756K V758D |
| Linum usitatissimum (flax) | E704K L708D |
|  | E719K L721D |
| Vitis vinifera (wine grape) | I652D |
| Oryza sativa Indica Group (Indian rice) | H759K I761D |
| Oryza sativa Japonica Group (Japanese rice) | Y780K N782D |
| Hordeum vulgare subsp. Vulgare (barley) | Y613K G615D |
|  | V636K |
| Zea mays (maize) | A676K E678D |
|  | A613K H615D |
| Oryza sativa (rice) | E1086K E1088D |
|  | Y1130K S1132D |
| Triticum aestivum (wheat) | M967K N969D |
|  | V628K |

Figure 11

| | Alignment | | species | gene | Pathogen | disease |
|---|---|---|---|---|---|---|
| (SEQ ID NO:11) | NLKE-PDLSLAINLEELDLVGCKSLVTLPSSIQNATKLIYLDMSDCKKLESFPTDL-NLE | 625 | Arabidopsis | SNC1 | Blumeria graminis | Powdery mildew |
| (SEQ ID NO:12) | NLK++ L+ +L L L G ++ LP+ I L LE+ + L L+ P+ + N<br>NLXDVGHLT----HLRYLGLEGT-NISKLPAEIGKLQFLEVLDLGNNHLKELPSTVCNFR | 683<br>656 | Barley | Mla1 | | |
| (SEQ ID NO:13) | LEELDLVGCKSLVTLPSSIQNATKLIYLDMSDCKKLSFPTDLNLESLEYL | 638 | Arabidopsis | SNC1 | Blumeria graminis | Powdery mildew |
| (SEQ ID NO:14) | LE LDL +++ LPS++ N +L+YL++ C+ + NL ++B L<br>LEVLDLGNNRNIKELPSTVCNFRRLGIYLNLVGCQVVPFVSLLQNLTAIEVL | 638<br>634 | Barley | Mla6 | | |
| (SEQ ID NO:15) | EMNLRYSNNLKEIPDLSLAINLEELDLVGCKSLVTLPSSIQNATKLIYLDMSDCKKLESF | 676 | Arabidopsis | SNC1 | Puccinia sorghi | leaf rust |
| (SEQ ID NO:16) | NL+++ L +N ++ C+ L +I T L++ + +K + +<br>-------NLRKLRHLGAYVNDFAIEKPIQLL-----NIGKLTSLQHIYVFSVQKKQGY | 707 | Maize | Rp1-D | | |
| (SEQ ID NO:17) | NLIMKYSKLEKLWEGTLPLGSLKEMNLRY----SNNLKEIPD-LSLAINLEELDLVGCKS | 648 | Arabidopsis | SNC1 | Puccinia sorghi | leaf rust |
| (SEQ ID NO:18) | +L+KY K +LPL K L Y N +P+ LS NL+ L ++ C<br>TILLKYITAE------SLPLFVSKFEYLGYLEISDVNCEALPEALSRCWNLQALHVLACSK | 621 | Maize | Rp3 | | |
| (SEQ ID NO:19) | KLWEGTLPLGSLKEMNLR------YSNNLKEIPDLSLAINLEELDLVGCK-SLVTLPSSTQ | 657 | Arabidopsis | SNC1 | Xanthomonas oryzae | bacterial blight |
| (SEQ ID NO:20) | + WEG L SLK+ + +S N +L L ++EEL+L GC +L+ L +<br>QEWEGFEQLTSLKKFRVTKCPEIFSTNF----ELFLPPSVEELELSGCNTILIQLSQLLV | 1104 | Rice | Xa1 | | |
| (SEQ ID NO:21) | NLEELDLVGCKSLVTLPSSIQNATKLIYLDMSDCKKLESFPPTDLNLESPPTDLNLESLEYLNLTGCPN | 695 | Arabidopsis | SNC1 | Magnaporthe grisea | Rice blast |
| (SEQ ID NO:22) | +L+ L L G +++ LSSS N L LD+ + T L++L+YL+ P+<br>HLKYLSLRGSAFTLNLPSSFGNLLNLETLDLVRGTWVIKLPATIGRLQNLKYLHRAGMPPD | 1185 | Rice | Pi-b | | |
| (SEQ ID NO:23) | SLKEMNLRYSNNLKEIPDLSLAINLEELDLVGCKSLVTLPSSIQNATKLIYLDMSDCKKL | 673 | Arabidopsis | SNC1 | Puccinia triticina | leaf rust |
| (SEQ ID NO:24) | +LK + + L P L +L L+L C S LP ++++ T L L + C -<br>NLKLLEIYGCSRLGPGPQLEAFPHLRMINLEDC-SWDALPGNLEHITSLKALKTERCMNI | 999 | wheat | Lr21 | | |
| (SEQ ID NO:25) | MKYSKLEKLWEGTLPLGSLKEMNLRYSNNMLKEIP-DLSLAINLEELDLVGCKSLVTLPSS | 655 | Arabidopsis | SNC1 | Blumeria graminis | Powdery mildew |
| (SEQ ID NO:26) | KY L L+ ++L S +K +P D+S+ NL+ LDL C L LP<br>PKY----------LHHLRYLDLSES-RMKALPEDLSILVMLQVLDLSYCNYLDRLPRQ | 643 | wheat | Pm3 | | |
| (SEQ ID NO:27) | KLWEGTLPLGSLKEMNLRYSNNLKEIPDLSLAINLEELDLVGCKSLVTLPSSIQNATKLI | 663 | Arabidopsis | SNC1 | Phytophthora infestans | late blight |
| (SEQ ID NO:28) | X+ G P LK + L Y + -K I NLE+L L GC- + +PS + I<br>KVSNGKFP--QLKLKLEYLSLVKWIVADDAFPNLEQLVLRGCQDLMEIPSCFMDILSLK | 1226 | potato | R1 | | |
| (SEQ ID NO:29) | ------LGSLKEMNLRYSNNLKEIP--DLSLAINLEELDLVGCKSLVT-PSSIQNATKLIYL | 665 | Arabidopsis | SNC1 | cladosporium fulvum | Leaf mould |
| (SEQ ID NO:30) | L SL K+++L + IP L NL L L G + +P I L YL<br>BEISYLRSLFELDLSDNALNGSIPASLGMMNNLSPLFLYGNQLSGSSIPEEICYLRSLTYL | 268 | tomato | Cf-2 | | |

SEQUENCE LISTING

```
<160> NUMBER OF SEQ ID NOS: 30

<210> SEQ ID NO 1
<211> LENGTH: 1301
<212> TYPE: PRT
<213> ORGANISM: Arabidopsis thaliana

<400> SEQUENCE: 1

Met Glu Ile Ala Ser Ser Ser Gly Ser Arg Arg Tyr Asp Val Phe Pro
1               5                   10                  15

Ser Phe Arg Gly Glu Asp Val Arg Asp Ser Phe Leu Ser His Leu Leu
            20                  25                  30

Lys Glu Leu Arg Gly Lys Ala Ile Thr Phe Ile Asp Asp Glu Ile Glu
        35                  40                  45

Arg Ser Arg Ser Ile Gly Pro Glu Leu Leu Ser Ala Ile Lys Glu Ser
    50                  55                  60

Arg Ile Ala Ile Val Ile Phe Ser Lys Asn Tyr Ala Ser Ser Thr Trp
65                  70                  75                  80

Cys Leu Asn Glu Leu Val Glu Ile His Lys Cys Tyr Thr Asn Leu Asn
                85                  90                  95

Gln Met Val Ile Pro Ile Phe Phe His Val Asp Ala Ser Glu Val Lys
            100                 105                 110
```

```
Lys Gln Thr Gly Glu Phe Gly Lys Val Phe Glu Thr Cys Lys Ala
            115                 120                 125

Lys Ser Glu Asp Glu Lys Gln Ser Trp Lys Gln Ala Leu Ala Ala Val
130                 135                 140

Ala Val Met Ala Gly Tyr Asp Leu Arg Lys Trp Pro Ser Glu Ala Ala
145                 150                 155                 160

Met Ile Glu Glu Leu Ala Glu Asp Val Leu Arg Lys Thr Met Thr Pro
            165                 170                 175

Ser Asp Asp Phe Gly Asp Leu Val Gly Ile Glu Asn His Ile Glu Ala
            180                 185                 190

Ile Lys Ser Val Leu Cys Leu Glu Ser Lys Glu Ala Arg Ile Met Val
            195                 200                 205

Gly Ile Trp Gly Gln Ser Gly Ile Gly Lys Ser Thr Ile Gly Arg Ala
            210                 215                 220

Leu Tyr Ser Lys Leu Ser Ile Gln Phe His His Arg Ala Phe Ile Thr
225                 230                 235                 240

Tyr Lys Ser Thr Ser Gly Ser Asp Val Ser Gly Met Lys Leu Arg Trp
            245                 250                 255

Glu Lys Glu Leu Leu Ser Glu Ile Leu Gly Gln Lys Asp Ile Lys Ile
            260                 265                 270

Glu His Phe Gly Val Val Glu Gln Arg Leu Lys Gln Gln Lys Val Leu
            275                 280                 285

Ile Leu Leu Asp Asp Val Asp Ser Leu Glu Phe Leu Lys Thr Leu Val
            290                 295                 300

Gly Lys Ala Glu Trp Phe Gly Ser Gly Ser Arg Ile Ile Val Ile Thr
305                 310                 315                 320

Gln Asp Arg Gln Leu Leu Lys Ala His Glu Ile Asp Leu Ile Tyr Glu
            325                 330                 335

Val Glu Phe Pro Ser Glu His Leu Ala Leu Thr Met Leu Cys Arg Ser
            340                 345                 350

Ala Phe Gly Lys Asp Ser Pro Pro Asp Phe Lys Glu Leu Ala Phe
            355                 360                 365

Glu Val Ala Lys Leu Ala Gly Asn Leu Pro Leu Gly Leu Ser Val Leu
            370                 375                 380

Gly Ser Ser Leu Lys Gly Arg Thr Lys Glu Trp Trp Met Glu Met Met
385                 390                 395                 400

Pro Arg Leu Arg Asn Gly Leu Asn Gly Asp Ile Met Lys Thr Leu Arg
                    405                 410                 415

Val Ser Tyr Asp Arg Leu His Gln Lys Asp Gln Asp Met Phe Leu Tyr
                    420                 425                 430

Ile Ala Cys Leu Phe Asn Gly Phe Glu Val Ser Tyr Val Lys Asp Leu
                    435                 440                 445

Leu Lys Asp Asn Val Gly Phe Thr Met Leu Thr Glu Lys Ser Leu Ile
450                 455                 460

Arg Ile Thr Pro Asp Gly Tyr Ile Glu Met His Asn Leu Leu Glu Lys
465                 470                 475                 480

Leu Gly Arg Glu Ile Asp Arg Ala Lys Ser Lys Gly Asn Pro Gly Lys
                    485                 490                 495

Arg Arg Phe Leu Thr Asn Phe Glu Asp Ile His Glu Val Val Thr Glu
                    500                 505                 510

Lys Thr Gly Thr Glu Thr Leu Leu Gly Ile Arg Leu Pro Phe Glu Glu
            515                 520                 525

Tyr Phe Ser Thr Arg Pro Leu Leu Ile Asp Lys Glu Ser Phe Lys Gly
```

```
            530                 535                 540
Met Arg Asn Leu Gln Tyr Leu Glu Ile Gly Tyr Tyr Gly Asp Leu Pro
545                 550                 555                 560

Gln Ser Leu Val Tyr Leu Pro Leu Lys Leu Arg Leu Leu Asp Trp Asp
                565                 570                 575

Asp Cys Pro Leu Lys Ser Leu Pro Ser Thr Phe Lys Ala Glu Tyr Leu
                580                 585                 590

Val Asn Leu Ile Met Lys Tyr Ser Lys Leu Glu Lys Leu Trp Glu Gly
                595                 600                 605

Thr Leu Pro Leu Gly Ser Leu Lys Glu Met Asn Leu Arg Tyr Ser Asn
                610                 615                 620

Asn Leu Lys Glu Ile Pro Asp Leu Ser Leu Ala Ile Asn Leu Glu Glu
625                 630                 635                 640

Leu Asp Leu Val Gly Cys Lys Ser Leu Val Thr Leu Pro Ser Ser Ile
                645                 650                 655

Gln Asn Ala Thr Lys Leu Ile Tyr Leu Asp Met Ser Asp Cys Lys Lys
                660                 665                 670

Leu Glu Ser Phe Pro Thr Asp Leu Asn Leu Glu Ser Leu Glu Tyr Leu
                675                 680                 685

Asn Leu Thr Gly Cys Pro Asn Leu Arg Asn Phe Pro Ala Ile Lys Met
                690                 695                 700

Gly Cys Ser Asp Val Asp Phe Pro Glu Gly Arg Asn Glu Ile Val Val
705                 710                 715                 720

Glu Asp Cys Phe Trp Asn Lys Asn Leu Pro Ala Gly Leu Asp Tyr Leu
                725                 730                 735

Asp Cys Leu Thr Arg Cys Met Pro Cys Glu Phe Arg Pro Glu Gln Leu
                740                 745                 750

Ala Phe Leu Asn Val Arg Gly Tyr Lys His Glu Lys Leu Trp Glu Gly
                755                 760                 765

Ile Gln Ser Leu Gly Ser Leu Glu Gly Met Asp Leu Ser Glu Ser Glu
                770                 775                 780

Asn Leu Thr Glu Ile Pro Asp Leu Ser Lys Ala Thr Lys Leu Glu Ser
785                 790                 795                 800

Leu Ile Leu Asn Asn Cys Lys Ser Leu Val Thr Leu Pro Ser Thr Ile
                805                 810                 815

Gly Asn Leu His Arg Leu Val Arg Leu Glu Met Lys Glu Cys Thr Gly
                820                 825                 830

Leu Glu Val Leu Pro Thr Asp Val Asn Leu Ser Ser Leu Glu Thr Leu
                835                 840                 845

Asp Leu Ser Gly Cys Ser Ser Leu Arg Ser Phe Pro Leu Ile Ser Thr
                850                 855                 860

Asn Ile Val Trp Leu Tyr Leu Glu Asn Thr Ala Ile Glu Glu Ile Pro
865                 870                 875                 880

Ser Thr Ile Gly Asn Leu His Arg Leu Val Arg Leu Glu Met Lys Lys
                885                 890                 895

Cys Thr Gly Leu Glu Val Leu Pro Thr Asp Val Asn Leu Ser Ser Leu
                900                 905                 910

Glu Thr Leu Asp Leu Ser Gly Cys Ser Ser Leu Arg Ser Phe Pro Leu
                915                 920                 925

Ile Ser Glu Ser Ile Lys Trp Leu Tyr Leu Glu Asn Thr Ala Ile Glu
                930                 935                 940

Glu Ile Pro Asp Leu Ser Lys Ala Thr Asn Leu Lys Asn Leu Lys Leu
945                 950                 955                 960
```

```
Asn Asn Cys Lys Ser Leu Val Thr Leu Pro Thr Thr Ile Gly Asn Leu
            965                 970                 975

Gln Lys Leu Val Ser Phe Glu Met Lys Glu Cys Thr Gly Leu Glu Val
        980                 985                 990

Leu Pro Ile Asp Val Asn Leu Ser  Ser Leu Met Ile Leu  Asp Leu Ser
        995                 1000                1005

Gly Cys Ser Ser Leu Arg Thr  Phe Pro Leu Ile Ser  Thr Asn Ile
    1010                1015                1020

Val Trp Leu Tyr Leu Glu Asn  Thr Ala Ile Glu Glu  Ile Pro Ser
    1025                1030                1035

Thr Ile Gly Asn Leu His Arg  Leu Val Lys Leu Glu  Met Lys Glu
    1040                1045                1050

Cys Thr Gly Leu Glu Val Leu  Pro Thr Asp Val Asn  Leu Ser Ser
    1055                1060                1065

Leu Met Ile Leu Asp Leu Ser  Gly Cys Ser Ser Leu  Arg Thr Phe
    1070                1075                1080

Pro Leu Ile Ser Thr Arg Ile  Glu Cys Leu Tyr Leu  Gln Asn Thr
    1085                1090                1095

Ala Ile Glu Glu Val Pro Cys  Cys Ile Glu Asp Phe  Thr Arg Leu
    1100                1105                1110

Thr Val Leu Met Met Tyr Cys  Cys Gln Arg Leu Lys  Thr Ile Ser
    1115                1120                1125

Pro Asn Ile Phe Arg Leu Thr  Arg Leu Glu Leu Ala  Asp Phe Thr
    1130                1135                1140

Asp Cys Arg Gly Val Ile Lys  Ala Leu Ser Asp Ala  Thr Val Val
    1145                1150                1155

Ala Thr Met Glu Asp His Val  Ser Cys Val Pro Leu  Ser Glu Asn
    1160                1165                1170

Ile Glu Tyr Ile Trp Asp Lys  Leu Tyr His Leu Pro  Ser Lys Leu
    1175                1180                1185

Asn Phe Asn Asp Val Glu Phe  Lys Phe Cys Cys Ser  Asn Arg Ile
    1190                1195                1200

Lys Glu Cys Gly Val Arg Leu  Met Tyr Val Ser Gln  Glu Glu Asn
    1205                1210                1215

Asn Gln Gln Thr Thr Arg Ser  Glu Lys Arg Met Arg  Met Thr Ser
    1220                1225                1230

Gly Thr Ser Glu Glu Asp Ile  Asn Leu Pro Tyr Gly  Leu Ile Val
    1235                1240                1245

Ala Asp Thr Gly Leu Ala Ala  Leu Asn Met Glu Leu  Ser Leu Gly
    1250                1255                1260

Gln Gly Glu Pro Ser Ser Ser  Thr Ser Leu Glu Gly  Glu Ala Leu
    1265                1270                1275

Cys Val Asp Tyr Met Ile Thr  Glu Glu Gln Asp Lys  Gly Ile Pro
    1280                1285                1290

Ile Leu Phe Pro Val Ser Gly  Asn
    1295                1300

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2
```

Glu Glu Leu Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Glu Lys Leu Asp
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Glu Arg Leu Asp
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct

<400> SEQUENCE: 5

Glu Tyr Val Asn
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Glu Lys Val Asn
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Construct

<400> SEQUENCE: 7

Glu Tyr Val Asp
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Construct

<400> SEQUENCE: 8

```
Glu Lys Val Asp
1
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is K or R

<400> SEQUENCE: 9

```
Glu Leu Xaa Leu Asp
1               5
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is K or Y
<220> FEATURE:
<221> NAME/KEY: MISC_FEATURE
<222> LOCATION: (6)..(6)
<223> OTHER INFORMATION: Xaa is N or D

<400> SEQUENCE: 10

```
Glu Leu Xaa Leu Val Xaa
1               5
```

<210> SEQ ID NO 11
<211> LENGTH: 59
<212> TYPE: PRT
<213> ORGANISM: Arabidopsis thaliana

<400> SEQUENCE: 11

```
Asn Leu Lys Glu Ile Pro Asp Leu Ser Leu Ala Ile Asn Leu Glu Glu
1               5                   10                  15

Leu Asp Leu Val Gly Cys Lys Ser Leu Val Thr Leu Pro Ser Ser Ile
            20                  25                  30

Gln Asn Ala Thr Lys Leu Ile Tyr Leu Asp Met Ser Asp Cys Lys Lys
        35                  40                  45

Leu Glu Ser Phe Pro Thr Asp Leu Asn Leu Glu
    50                  55
```

<210> SEQ ID NO 12
<211> LENGTH: 56
<212> TYPE: PRT
<213> ORGANISM: Hordeum vulgare

<400> SEQUENCE: 12

```
Asn Leu Lys Asp Val Gly His Leu Thr His Leu Arg Tyr Leu Gly Leu
1               5                   10                  15

Glu Gly Thr Asn Ile Ser Lys Leu Pro Ala Glu Ile Gly Lys Leu Gln
            20                  25                  30

Phe Leu Glu Val Leu Asp Leu Gly Asn Asn His Asn Leu Lys Glu Leu
        35                  40                  45

Pro Ser Thr Val Cys Asn Phe Arg
    50                  55
```

```
            50                  55

<210> SEQ ID NO 13
<211> LENGTH: 51
<212> TYPE: PRT
<213> ORGANISM: Arabidopsis thaliana

<400> SEQUENCE: 13

Leu Glu Glu Leu Asp Leu Val Gly Cys Lys Ser Leu Val Thr Leu Pro
1               5                   10                  15

Ser Ser Ile Gln Asn Ala Thr Lys Leu Ile Tyr Leu Asp Met Ser Asp
            20                  25                  30

Cys Lys Lys Leu Glu Ser Phe Pro Thr Asp Leu Asn Leu Glu Ser Leu
        35                  40                  45

Glu Tyr Leu
    50

<210> SEQ ID NO 14
<211> LENGTH: 51
<212> TYPE: PRT
<213> ORGANISM: Hordeum vulgare

<400> SEQUENCE: 14

Leu Glu Val Leu Asp Leu Gly Asn Asn Arg Asn Ile Lys Glu Leu Pro
1               5                   10                  15

Ser Thr Val Cys Asn Phe Arg Arg Leu Ile Tyr Leu Asn Leu Val Gly
            20                  25                  30

Cys Gln Val Val Pro Pro Val Gly Leu Leu Gln Asn Leu Thr Ala Ile
        35                  40                  45

Glu Val Leu
    50

<210> SEQ ID NO 15
<211> LENGTH: 60
<212> TYPE: PRT
<213> ORGANISM: Arabidopsis thaliana

<400> SEQUENCE: 15

Glu Met Asn Leu Arg Tyr Ser Asn Asn Leu Lys Glu Ile Pro Asp Leu
1               5                   10                  15

Ser Leu Ala Ile Asn Leu Glu Gly Leu Asp Leu Val Gly Cys Lys Ser
            20                  25                  30

Leu Val Thr Leu Pro Ser Ser Ile Gln Asn Ala Thr Lys Leu Ile Tyr
        35                  40                  45

Leu Asp Met Ser Asp Cys Lys Lys Leu Glu Ser Phe
    50                  55                  60

<210> SEQ ID NO 16
<211> LENGTH: 47
<212> TYPE: PRT
<213> ORGANISM: Zea mays

<400> SEQUENCE: 16

Asn Leu Arg Lys Leu Arg His Leu Gly Ala Tyr Val Asn Asp Phe Ala
1               5                   10                  15

Ile Glu Lys Pro Ile Cys Gln Ile Leu Asn Ile Gly Lys Leu Thr Ser
            20                  25                  30

Leu Gln His Ile Tyr Val Phe Ser Val Gln Lys Lys Gln Gly Tyr
        35                  40                  45
```

<210> SEQ ID NO 17
<211> LENGTH: 55
<212> TYPE: PRT
<213> ORGANISM: Arabidopsis thaliana

<400> SEQUENCE: 17

Asn Leu Ile Met Lys Tyr Ser Lys Leu Glu Lys Leu Trp Glu Gly Thr
1               5                   10                  15
Leu Pro Leu Gly Ser Leu Lys Glu Met Asn Leu Arg Tyr Ser Asn Asn
            20                  25                  30
Leu Lys Glu Ile Pro Asp Leu Ser Leu Ala Ile Asn Leu Glu Glu Leu
        35                  40                  45
Asp Leu Val Gly Cys Lys Ser
    50                  55

<210> SEQ ID NO 18
<211> LENGTH: 55
<212> TYPE: PRT
<213> ORGANISM: Zea mays

<400> SEQUENCE: 18

Thr Ile Ile Leu Lys Tyr Ile Thr Ala Glu Ser Leu Pro Leu Phe Val
1               5                   10                  15
Ser Lys Phe Glu Tyr Leu Gly Tyr Leu Glu Ile Ser Asp Val Asn Cys
            20                  25                  30
Glu Ala Leu Pro Glu Ala Leu Ser Arg Cys Trp Asn Leu Gln Ala Leu
        35                  40                  45
His Val Leu Ala Cys Ser Lys
    50                  55

<210> SEQ ID NO 19
<211> LENGTH: 54
<212> TYPE: PRT
<213> ORGANISM: Arabidopsis thaliana

<400> SEQUENCE: 19

Lys Leu Trp Glu Gly Thr Leu Pro Leu Gly Ser Leu Lys Glu Met Asn
1               5                   10                  15
Leu Arg Tyr Ser Asn Asn Leu Lys Glu Ile Pro Asp Leu Ser Leu Ala
            20                  25                  30
Ile Asn Leu Glu Glu Leu Asp Leu Val Gly Cys Lys Ser Leu Val Thr
        35                  40                  45
Leu Pro Ser Ser Ile Gln
    50

<210> SEQ ID NO 20
<211> LENGTH: 56
<212> TYPE: PRT
<213> ORGANISM: Oryza sativa

<400> SEQUENCE: 20

Gln Phe Trp Glu Gly Phe Glu Gln Leu Thr Ser Leu Lys Lys Phe Arg
1               5                   10                  15
Val Ile Lys Cys Pro Glu Ile Phe Ser Thr Asn Phe Gly Leu Phe Leu
            20                  25                  30
Pro Pro Ser Val Glu Glu Leu Glu Leu Ser Gly Cys Asn Ile Thr Leu
        35                  40                  45
Ile Gln Leu Ser Gln Leu Leu Val
    50                  55

<210> SEQ ID NO 21
<211> LENGTH: 59
<212> TYPE: PRT
<213> ORGANISM: Arabidopsis thaliana

<400> SEQUENCE: 21

Asn Leu Glu Glu Leu Asp Leu Val Gly Cys Lys Ser Leu Val Thr Leu
1               5                   10                  15

Pro Ser Ser Ile Gln Asn Ala Thr Lys Leu Ile Tyr Leu Asp Met Ser
            20                  25                  30

Asp Cys Lys Lys Leu Glu Ser Phe Pro Thr Asp Leu Asn Leu Glu Ser
        35                  40                  45

Leu Glu Tyr Leu Asn Leu Thr Gly Cys Pro Asn
    50                  55

<210> SEQ ID NO 22
<211> LENGTH: 59
<212> TYPE: PRT
<213> ORGANISM: Oryza sativa

<400> SEQUENCE: 22

His Leu Lys Tyr Leu Ser Leu Arg Gly Ser Ala Thr Ile Leu Asn Leu
1               5                   10                  15

Pro Ser Ser Phe Gly Asn Leu Leu Asn Leu Glu Thr Leu Asp Ile Arg
            20                  25                  30

Gly Thr Trp Val Thr Lys Leu Pro Ala Thr Ile Gly Arg Leu Gln Asn
        35                  40                  45

Leu Lys Tyr Leu His Ala Gly Met Pro Pro Asp
    50                  55

<210> SEQ ID NO 23
<211> LENGTH: 60
<212> TYPE: PRT
<213> ORGANISM: Arabidopsis thaliana

<400> SEQUENCE: 23

Ser Leu Lys Glu Met Asn Leu Arg Tyr Ser Asn Leu Lys Glu Ile
1               5                   10                  15

Pro Asp Leu Ser Leu Ala Ile Asn Leu Glu Glu Leu Asp Leu Val Gly
            20                  25                  30

Cys Lys Ser Leu Val Thr Leu Pro Ser Ser Ile Gln Asn Ala Thr Lys
        35                  40                  45

Leu Ile Tyr Leu Asp Met Ser Asp Cys Lys Lys Leu
    50                  55                  60

<210> SEQ ID NO 24
<211> LENGTH: 59
<212> TYPE: PRT
<213> ORGANISM: Triticum aestivum

<400> SEQUENCE: 24

Asn Leu Lys Leu Leu Glu Ile Thr Gly Cys Ser Arg Leu Gly Pro Gly
1               5                   10                  15

Pro Gln Leu Glu Ala Phe Pro His Leu Arg Met Leu Asn Leu Glu Asp
            20                  25                  30

Cys Ser Trp Asp Ala Leu Pro Gly Asn Leu Glu His Leu Thr Ser Leu
        35                  40                  45

Lys Ala Leu Lys Ile Glu His Cys Met Asn Ile 50              55

<210> SEQ ID NO 25
<211> LENGTH: 59
<212> TYPE: PRT
<213> ORGANISM: Arabidopsis thaliana

<400> SEQUENCE: 25

Met Lys Tyr Ser Lys Leu Glu Lys Leu Trp Glu Gly Thr Leu Pro Leu
1               5                   10                  15

Gly Ser Leu Lys Glu Met Asn Leu Arg Tyr Ser Asn Asn Leu Lys Glu
            20                  25                  30

Ile Pro Asp Leu Ser Leu Ala Ile Asn Leu Glu Glu Leu Asp Leu Val
        35                  40                  45

Gly Cys Lys Ser Leu Val Thr Leu Pro Ser Ser
    50                  55

<210> SEQ ID NO 26
<211> LENGTH: 47
<212> TYPE: PRT
<213> ORGANISM: Triticum aestivum

<400> SEQUENCE: 26

Pro Lys Tyr Leu His His Leu Arg Tyr Leu Asp Leu Ser Glu Ser Arg
1               5                   10                  15

Met Lys Ala Leu Pro Glu Asp Ile Ser Ile Leu Tyr Asn Leu Gln Val
            20                  25                  30

Leu Asp Leu Ser Tyr Cys Asn Tyr Leu Asp Arg Leu Pro Arg Gln
        35                  40                  45

<210> SEQ ID NO 27
<211> LENGTH: 60
<212> TYPE: PRT
<213> ORGANISM: Arabidopsis thaliana

<400> SEQUENCE: 27

Lys Leu Trp Glu Gly Thr Leu Pro Leu Gly Ser Leu Lys Glu Met Asn
1               5                   10                  15

Leu Arg Tyr Ser Asn Asn Leu Lys Glu Ile Pro Asp Leu Ser Leu Ala
            20                  25                  30

Ile Asn Leu Glu Glu Leu Asp Leu Val Gly Cys Lys Ser Leu Val Thr
        35                  40                  45

Leu Pro Ser Ser Ile Gln Asn Ala Thr Lys Leu Ile
    50                  55                  60

<210> SEQ ID NO 28
<211> LENGTH: 58
<212> TYPE: PRT
<213> ORGANISM: Solanum tuberosum

<400> SEQUENCE: 28

Lys Val Ser Asn Gly Lys Phe Pro Gln Leu Lys Ile Leu Lys Leu Glu
1               5                   10                  15

Tyr Leu Ser Leu Val Lys Trp Ile Val Ala Asp Asp Ala Phe Pro Asn
            20                  25                  30

Leu Glu Gln Leu Val Leu Arg Gly Cys Gln Asp Leu Met Glu Ile Pro
        35                  40                  45

Ser Cys Phe Met Asp Ile Leu Ser Leu Lys
    50                  55

```
<210> SEQ ID NO 29
<211> LENGTH: 54
<212> TYPE: PRT
<213> ORGANISM: Arabidopsis thaliana

<400> SEQUENCE: 29

Leu Gly Ser Leu Lys Glu Met Asn Leu Arg Tyr Ser Asn Asn Leu Lys
1               5                   10                  15

Glu Ile Pro Asp Leu Ser Leu Ala Ile Asn Leu Glu Glu Leu Asp Leu
            20                  25                  30

Val Gly Cys Lys Ser Leu Val Thr Leu Pro Ser Ser Ile Gln Asn Ala
        35                  40                  45

Thr Lys Leu Ile Tyr Leu
    50

<210> SEQ ID NO 30
<211> LENGTH: 60
<212> TYPE: PRT
<213> ORGANISM: Lycopersicon esculentum

<400> SEQUENCE: 30

Glu Glu Ile Ser Tyr Leu Arg Ser Leu Thr Glu Leu Asp Leu Ser Asp
1               5                   10                  15

Asn Ala Leu Asn Gly Ser Ile Pro Ala Ser Leu Gly Asn Met Asn Asn
            20                  25                  30

Leu Ser Phe Leu Phe Leu Tyr Gly Asn Gln Leu Ser Gly Ser Ile Pro
        35                  40                  45

Glu Glu Ile Cys Tyr Leu Arg Ser Leu Thr Tyr Leu
    50                  55                  60
```

ENGINEERING HEAT-STABLE DISEASE RESISTANCE IN PLANTS

CROSS-REFERENCE TO RELATED APPLICATIONS

This application is the U.S. National Stage filing under 35 U.S.C. §371 of International Application No. PCT/US2009/069082, filed Dec. 21, 2009, which claims benefit of U.S. Provisional Patent Application No. 61/139,369, filed Dec. 19, 2008.

STATEMENT AS TO FEDERALLY FUNDED RESEARCH

This work was supported by grant number 2005-35100-16044 from the United States Department of Agriculture. The Government has certain rights in the invention.

BACKGROUND OF THE INVENTION

The invention relates to plant disease resistance.

Plant diseases cause crop losses that are devastating to world food supply and human well being. Plants have evolved defense mechanisms to ward off diverse biotic attacks to ensure their survival and fitness. This plant immunity occurs at multiple levels and can be largely divided into two branches (1, 31). One is a general resistance responding to molecules common to many pathogens and the other is a 'cultivar-specific' resistance responding to pathogen virulent factors. The latter resistance is induced upon a specific recognition of the pathogen race-specific avirulence (Avr) gene by the disease resistance (R) gene of the host plant (32). This 'gene-for-gene' interaction leads to rapid and efficient defense responses including a form of programmed cell death named hypersensitive response (HR) to restrict the growth of pathogens (33). A number of R genes have been molecularly cloned in many species and the largest class of R proteins contains 'nucleotide-binding' (NB) and leucine-rich repeat (LRR) domains (8, 9). A direct or indirect interaction between Avr proteins and the R proteins activates downstream signaling events leading to local HR and systemic acquired resistance throughout plants.

Plant defense responses are modulated by a number of environmental factors including light, humidity, and temperature. Temperature variations influence disease resistance to bacteria, fungi, virus, and insects (34). A high temperature often suppresses disease resistance in plants, and this phenomenon is named 'heat masking'. This heat sensitivity has been reported in a number of disease resistance responses mediated by R genes such as the N gene in tobacco (35), Mi in tomato (6), RPW8 in *Arabidopsis* (36), and SNC1 in *Arabidopsis* (7).

There is accordingly a need in the art for plants having increased tolerance to temperature thereby avoiding high temperature-suppression of a resistance response. Genes conferring temperature insensitivity are consequently needed for disease resistance management at high temperatures. The present invention provides such genes and includes methods for conferring disease resistance to plants at temperatures at which defense responses are typically diminished or masked due to heat sensitivity.

SUMMARY OF THE INVENTION

It has been found that temperature modulates plant defense responses through disease resistance proteins. As is described below, through a genetic screen, a causal temperature sensitive component in plant disease resistance has been identified, and this component is a NB-LRR type of R-like gene SNC1 from a crucifer, *Arabidopsis thaliana*. In particular, specific mutant forms of SNC1 have been demonstrated to induce heat-stable disease resistance. Demonstrating the general applicability of this discovery, similar modifications created in another R gene N were also shown to confer heat-stable disease resistance to tobacco mosaic virus. This discovery provides a methodology to engineer or breed plants or both with an ability to mount defense responses over a range of temperatures.

In general, the invention features an isolated nucleic acid molecule which includes a nucleotide sequence encoding a polypeptide including: (a) a nucleotide binding (NB) domain; and (b) a leucine rich repeat (LRR) domain, wherein the polypeptide confers a heat-stable defense response to a plant pathogen. In one example, the polypeptide includes an LRR domain that includes a sub-domain that confers the heat stable defense response. In preferred embodiments, the LRR domain that confers a heat-stable defense response to a plant pathogen includes an E/L(K or R)LD motif or an E/L(K or Y)LV(N or D) motif.

In other preferred embodiments, the nucleotide sequence is operably linked to a promoter that drives expression in a plant cell. Useful promoters include constitutive promoters, inducible promoters, or a tissue-specific promoter. In preferred embodiments, tissue-specific promoters include root-, leaf-, or seed-specific promoters. Exemplary promoters are described herein. In other preferred embodiments, the isolated nucleic acid molecule is composed, either wholly or partially, of synthetic nucleotide building blocks. In still other preferred embodiments, codon usage of the nucleotide sequence is optimized for expression in a plant.

In preferred embodiments, the expressed polypeptide confers disease resistance on a plant expressing the polypeptide at both 22° C. and 28° C. or at both 22° C. and 30° C. In other embodiments, the expressed polypeptide confers disease resistance on a plant expressing the polypeptide at 23° C., 24° C., 25° C., 26° C., 27° C., 28° C., 29° C., 30° C., 31° C., 32° C., 33° C., 34° C., 35° C., 36° C. or a higher temperature.

In other aspects, the invention features a vector, a cell, or a plant or plant component which includes any of the aforementioned isolated nucleic acid molecules. Exemplary vectors, cells, and plants are described herein.

In still other aspects, the invention features a method of conferring resistance to a pathogen in a plant or a plant component, the method includes the steps of: (a) transforming a plant cell with an isolated nucleic acid molecule that encodes a polypeptide which includes: (i) a NB domain; and (ii) a LRR domain, wherein the polypeptide confers a heat-stable defense response to a plant pathogen; and (b) regenerating a plant or plant component from the transformed plant cell, wherein the plant or plant component exhibits resistance to the pathogen. In one example, the polypeptide includes an LRR domain that confers the heat stable defense response. In preferred embodiments, the expressed polypeptide confers disease resistance on a plant expressing said polypeptide at a wide range of temperature (such as 23° C., 24° C., 25° C., 26° C., 27° C., 28° C., 29° C., 30° C., 31° C., 32° C., 33° C., 34° C., 35° C., 36° C. or a higher temperature).

In other preferred embodiments, the plant expressing the heat-stable NB-LRR polypeptide has an increased level of resistance compared to a corresponding control plant at an elevated temperature of the control plant.

In still other embodiments, the nucleic acid molecule is introduced through breeding or through transformation or both. Preferably, the plant is a monocot or a dicot and the pathogen is a bacterial, fungal, nematode, insect, or a viral pathogen. Exemplary plants useful in the invention include, without limitation, crucifers such as *Arabidopsis thaliana*, *Populus trichocarpa* (black cottonwood), *Solanum tuberosum* (potatoes), *Cucumis melo* (Oriental melon), *Medicago sativa* (alfalfa), *Populus balsamifera* (balsam poplar), *Phaseolus vulgaris* (French bean), *Glycine max* (soybeans), *Medicago truncatula, Nicotiana tabacum* (tobacco), *Nicotiana glutinosa, Solanum lycopersicum* (tomato), *Solanum tuberosum* subsp. *andigena* (potato), *Lens culinaris* (lentil), *Linum usitatissimum* (flax), *Vitis vinifera* (wine grape), *Oryza sativa* Indica Group (Indian rice), or *Oryza sativa* Japonica Group (Japanese rice), *Zea mays* (corn), (barley), and (wheat).

In another aspect, the invention features a substantially-pure polypeptide which includes: (a) a NB domain; and (b) a LRR domain, wherein the polypeptide confers a heat-stable defense response to a plant pathogen. Preferably, the polypeptide confers disease resistance on a plant expressing said polypeptide at both 22° C. and 28° C. or at both 22° C. and 30° C. In one example, the substantially-pure polypeptide includes an LRR domain that confers the heat-stable defense response. In other embodiments, the substantially-pure polypeptide confers disease resistance on a plant expressing the polypeptide at 23° C., 24° C., 25° C., 26° C., 27° C., 28° C., 29° C., 30° C., 31° C., 32° C., 33° C., 34° C., 35° C., 36° C. or a higher temperature.

By "heat-stable defense response" is meant a NB-LRR polypeptide mediated pathogen defense response in a plant which occurs at a temperature at which the plant fails to mount the pathogen defense response in its absence. Such a temperature is higher than the temperature at which the plant mounts the pathogen defense response without the presence of the polypeptide. For example, a heat-stable defense response is preferably 2° C., 3° C., 4° C., or even 5° C. higher than the temperature at which the plant fails to mount the pathogen defense response in the absence of the polypeptide; more preferably, the heat-stable defense response is 6° C., 7° C., or even 8° C. higher than the temperature at which the plant fails to mount the pathogen defense response in the absence of the polypeptide; and most preferably, the heat-stable defense response is 9° C., 10° C., or 11° C. (or even 12° C. or more) higher than the temperature at which the plant fails to mount the pathogen defense response in the absence of the polypeptide.

By a "substantially pure polypeptide" is meant a polypeptide such as a heat-stable NB-LRR disease resistance polypeptide (for example, a SNC1-3, SNC1 E640R, N Y646K, or N Y638K N648D polypeptide or a polypeptide described in FIG. 9 or FIG. 10) that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a heat-stable NB-LRR disease resistance polypeptide. A substantially pure heat-stable NB-LRR disease resistance polypeptide may be obtained, for example, by extraction from a natural source (for example, a plant cell); by expression of a recombinant nucleic acid encoding a heat-stable NB-LRR disease resistance polypeptide; or by chemically synthesizing the protein. Purity can be measured by any appropriate method, for example, column chromatography, polyacrylamide gel electrophoresis, or by HPLC analysis.

By "isolated nucleic acid molecule" is meant a nucleic acid molecule that is free of the genes which, in the naturally-occurring genome of the organism from which the nucleic acid molecule is derived from, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. It also includes a recombinant DNA which is part of a hybrid gene encoding additional polypeptide sequence.

By "derived from" is meant isolated from or having the sequence of a naturally-occurring sequence (for example, a cDNA, genomic DNA, synthetic DNA, or combination thereof).

By "masking temperature" is meant a temperature at which a defense response to a pathogen is ineffective to provide a plant with resistance to such pathogen.

By "polypeptide" or "protein" is meant any chain of amino acids, regardless of length or post-translational modification (for example, glycosylation or phosphorylation).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "plant component" is meant a part, segment, or organ obtained from an intact plant or plant cell. Exemplary plant components include, without limitation, somatic embryos, leaves, stems, roots, flowers, tendrils, fruits, scions, seeds, and rootstocks.

By "crucifer" is meant any plant that is classified within the Cruciferae family. The Cruciferae include many agricultural crops, including, without limitation, rape (for example, *Brassica campestris* and *Brassica napus*), broccoli, cabbage, brussel sprouts, radish, kale, Chinese kale, kohlrabi, cauliflower, turnip, rutabaga, mustard, horseradish, and *Arabidopsis*.

By "transgene" is meant any piece of a nucleic acid molecule (e.g., DNA) which is inserted by artifice into a cell, and becomes part of the genome of the organism which develops from that cell. Such a transgene may include a gene which is partly or entirely heterologous (i.e., foreign) to the transgenic organism, or may represent a gene having sequence identity to an endogenous gene of the organism.

By "transgenic" is meant any cell which includes an isolated nucleic acid molecule (e.g., a DNA sequence) which is inserted by artifice into a cell and becomes part of the genome of the organism which develops from that cell. As used herein, the transgenic organisms are generally transgenic plants and the DNA (for example, a transgene) is inserted by artifice into the nuclear or plastidic genome. A transgenic plant according to the invention may contain one or more of the isolated nucleic acid molecules described herein.

By "pathogen" is meant an organism whose infection of viable plant tissue elicits a disease response in the plant tissue. Such pathogens include, without limitation, bacteria, mycoplasmas, fungi, oomycetes, insects, nematodes, viruses, and viroids. Examples of such plant diseases caused by these pathogens are described in Chapters 11-16 of Agrios, *Plant Pathology*, 3rd ed., Academic Press, Inc., New York, 1988.

Examples of bacterial pathogens include, without limitation, *Erwinia* (for example, *E. carotovora*), *Pseudomonas* (for example, *P. syringae*), and *Xanthomonas* (for example, *X. campepestris* and *X. oryzae*).

Examples of fungal or fungal-like disease-causing pathogens include, without limitation, *Alternaria* (for example, *A. brassicola* and *A. solani*), *Ascochyta* (for example, *A. pisi*), *Botrytis* (for example, *B. cinerea*), *Cercospora* (for example, *C. kikuchii* and *C. zaea-maydis*), *Colletotrichum* sp. (for example, *C. lindemuthianum*), *Diplodia* (for example, *D. maydis*), *Erysiphe* (for example, *E. graminis* f.sp. *graminis* and *E. graminis* f.sp. *hordei*), *Fusarium* (for example, *F. nivale* and *F. oxysporum, F. graminearum, F. solani, F. monilforme*, and *F. roseum*), *Gaeumanomyces* (for example, *G. graminis* f.sp. *tritici*), *Helminthosporium* (for example, *H. turcicum, H. carbonum*, and *H. maydis*), *Macrophomina* (for example, *M. phaseolina* and *Maganaporthe grisea*), *Nectria* (for example, *N. heamatocacca*), *Peronospora* (for example, *P. manshurica, P. tabacina*), *Phoma* (for example, *P. betae*), *Phymatotrichum* (for example, *P. omnivorum*), *Phytophthora* (for example, *P. cinnamomi, P. cactorum, P. phareoli, P. parasitica, P. citrophthora, P. megasperma* f.sp. *sojae*, and *P. infestans*), *Plasmopara* (for example, *P. viticola*), *Podosphaera* (for example, *P. leucotricha*), *Puccinia* (for example, *P. sorghi, P. striiformis, P. graminis* f.sp. *tritici, P. asparagi, P. recondita*, and *P. arachidis*), *Puthium* (for example, *P. aphanidermatum*), *Pyrenophora* (for example, *P. tritici-repentens*), *Pyricularia* (for example, *P. oryzea*), *Pythum* (for example, *P. ultimum*), *Rhizoctonia* (for example, *R. solani* and *R. cerealis*), *Scerotium* (for example, *S. rolfsii*), *Sclerotinia* (for example, *S. sclerotiorum*), *Septoria* (for example, *S. lycopersici, S. glycines, S. nodorum* and *S. tritici*), *Thielaviopsis* (for example, *T. basicola*), *Uncinula* (for example, *U. necator*), *Venturia* (for example, *V. inaequalis*), and *Verticillium* (for example, *V. dahliae* and *V. albo-atrum*).

Examples of pathogenic nematodes include, without limitation, root-knot nematodes (for example, *Meloidogyne* sp. such as *M. incognita, M. arenaria, M. chitwoodi, M. hapla, M. javanica, M. graminocola, M. microtyla, M. graminis*, and *M. naasi*), cyst nematodes (for example, *Heterodera* sp. such as *H. schachtlii, H. glycines, H. sacchari, H. oryzae, H. avenae, H. cajani, H. elachista, H. goettingiana, H. graminis, H. mediterranea, H. mothi, H. sorghi*, and *H. zeae*, or, for example, *Globodera* sp. such as *G. rostochiensis* and *G. pallida*), root-attacking nematodes (for example, *Rorylenchulus reniformis, Tylenchuylus semipenetrans, Pratylenchus brachyurus, Radopholus citrophilus, Radopholus similis, Xiphinema americanum, Xiphinema rivesi, Paratrichodorus minor, Heterorhabditis hellothidis*, and *Bursaphelenchus xylophilus*), and above-ground nematodes (for example, *Anguina funesta, Anguina tritici, Ditylenchus dipsaci, Ditylenchus myceliphagus*, and *Aphenlenchoides besseyi*).

Examples of viral pathogens include, without limitation, tobacco mosaic virus (TMV), tobacco necrosis virus (TNV), potato leaf roll virus, potato virus X, potato virus Y, tomato spotted wilt virus, and tomato ring spot virus.

As discussed herein, several genes encoding heat-stable NB-LRR disease resistance polypeptides has been identified, isolated or engineered, and characterized. Accordingly, the invention provides a number of important advances and advantages for the protection of plants against pathogens. For example, the invention facilitates an effective and economical means for in-plant protection against plant pathogens at temperatures at which heat masking or sensitivity to heat occurs. Such protection against pathogens reduces or minimizes the need for traditional chemical practices (for example, application of fungicides, bactericides, nematicides, insecticides, or viricides) that are typically used by farmers for controlling the spread of plant pathogens and providing protection against disease-causing pathogens. In addition, because plants which include heat-stable NB-LRR disease resistance polypeptides are less vulnerable to pathogens and their diseases, the invention further provides for increased production efficiency, as well as for improvements in quality and yield of crop plants and ornamentals. Thus, the invention contributes to the production of high quality and high yield agricultural products, for example, fruits, ornamentals, vegetables, cereals and field crops having reduced spots, blemishes, and blotches that are caused by pathogens; agricultural products with increased shelf-life and reduced handling costs; and high quality and yield crops for agricultural (for example, cereal and field crops), industrial (for example, oilseeds), and commercial (for example, fiber crops) purposes. Furthermore, because the invention reduces the necessity for chemical protection against plant pathogens, the invention benefits the environment where the crops are grown. Genetically-improved seeds and other plant products that are produced using plants expressing the genes described herein also render farming possible in areas previously unsuitable for agricultural production due to, for example, temperature extremes and global climate change.

Constructs

As is discussed above, the invention relates to vectors, especially plasmids, and other vectors common in genetic engineering, that contain the above-described isolated nucleic acid molecules encoding a heat-stable NB-LRR polypeptide. Preferably, such nucleic acid molecules contained in the vectors are operably linked to regulatory elements that provide for the transcription and expression of a polypeptide or protein in eukaryotic cells. Typically, the recombinant DNA molecule containing the isolated nucleic acid molecule will include in an operably linked manner, in the 5' to 3' direction of transcription, a transcription initiation control region capable of promoting, initiating and/or modulating transcription and translation in a plant cell (a promoter region), the nucleic acid molecule encoding a heat-stable NB-LRR polypeptide, and a transcription and translation termination region (otherwise referred to as a 3' untranslated region). As used herein, a first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. A "recombinant" nucleic acid or "recombinant DNA molecule" is made by an artificial combination of two otherwise separated segments of sequence, e.g., by chemical synthesis or by the manipulation of isolated segments of nucleic acids by genetic engineering techniques. The terms "recombinant DNA construct," "recombinant vector," "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

As used herein, a "promoter" refers to a DNA sequence that binds an RNA polymerase (and often other transcription factors as well) and promotes transcription of a downstream DNA sequence. The resulting transcribed sequence can be an RNA that has function, such as rRNA (ribosomal RNA) or tRNA (transfer RNA). Often, the RNA produced is a heteronuclear (hn) RNA that has introns that are spliced out to produce an mRNA (messenger RNA). A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Specific expression is used herein to refer to any promoter that provides an increased expression in a single tissue or developmental stage, or under a particular environmental condition, but causes expression, even significant expression, in other tissue(s), or developmental stage(s), or environmental condition(s).

Temporally regulated promoters are functional only or predominantly during certain periods of plant development or at certain times of day. Inducible promoters selectively express an operably linked DNA sequence in response to the presence of an endogenous or exogenous stimulus, for example, by chemical compounds (chemical inducers) or in response to environmental, hormonal, chemical, and/or developmental signals. Inducible or regulated promoters include, for example, promoters regulated by light, heat, stress, flooding or drought, phytohormones, wounding, cold, or chemicals such as ethanol, jasmonate, salicylic acid, or safeners.

For the most part, any plant promoter can be used as a 5' regulatory sequence to modulate expression of a particular gene or genes, such as a plant RNA polymerase II promoter. When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences). Alternatively, heterologous regulatory sequences can be added to the 5' upstream region of an inactive, truncated promoter, e.g., a promoter including only the core TATA and, sometimes, the CCAAT sequences.

Promoters include distinct cis-acting transcriptional regulatory elements, which can confer a different aspect of the overall control of gene expression. The promoter sequences of the present invention may contain cis elements that modulate gene expression. Cis elements can be part of the promoter, or can be upstream or downstream of said promoter. Cis elements (or groups thereof), acting at a distance from a promoter are often referred to as repressors or enhancers. Enhancers act to upregulate the transcriptional initiation rate of RNA polymerase at a promoter, while repressors act to decrease said rate. In some cases, the same elements can be found in a promoter and an enhancer or repressor. Cis elements are generally sites where transcription factors bind to the DNA and modulate the rate at which RNA polymerase binds to the promoter.

Examples of constitutive promoters that are active in plant cells include but are not limited to the nopaline synthase (NOS) promoters; the cauliflower mosaic virus (CaMV) 19S and 35S (sometimes called 35S herein); the tobacco mosaic virus promoter; the figwort mosaic virus promoters; and actin promoters, such as the *Arabidopsis* actin gene promoter.

The term "tissue-specific promoter" means a regulatory sequence that causes an enhancement of transcription from a downstream gene in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, style-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to expression in other tissues as well.

In a preferred embodiment of the invention, the nucleic acid molecule encoding a heat-stable NB-LRR polypeptide is operably linked to a tissue-specific promoter, or promoter that directs expression in the leaf tissue or a region therein.

Other examples of possible suitable regulatory sequences include introns, 3' non-coding regions such as poly A sequences, insulator regions and the like. Molecular biological techniques for identifying, obtaining and using such regulatory elements in combination with the nucleic acid molecules of the present invention are known in the art.

Transformation Methods and Transgenic Plants or Plant Components

The present invention further relates to transgenic plant cells and transgenic plants having been transformed to contain and express a heat-stable NB-LRR polypeptide. "Transformed," "transfected," or "transgenic" refers to a cell, tissue, organ, or organism into which has been introduced a foreign nucleic acid, such as a recombinant vector. A transgenic plant according to the invention may contain one or more of the nucleic acid molecules described herein. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector. The method of transformation is not critical to the current invention and various methods of plant transformation are currently known and available. For example, the introduction of DNA sequences into plants and/or plant cells can be accomplished by *Agrobacterium* mediated transformation, viral vector mediated transformation, electroporation, and microprojectile bombardment mediated transformation (particle gun or biolistics methods). The DNA sequence may also be transformed directly into the plastid genome by plastid transformation.

Floral dip transformation is also useful for introducing a construct into a plant. Here *Agrobacterium* carrying a genetic construct is applied to a flowering plant such as *Arabidopsis* that subsequently set seeds, and transgenic plants are then selected among the progeny seedlings according to standard methods.

Whole plants can be regenerated, for example, from single cells, callus tissue, or leaf discs transformed with a plant expression vector according to standard plant tissue culture techniques. It is well known in the art that various cells, tissues, and organs from almost any plant can be successfully cultured to regenerate an entire plant; according to standard techniques.

This invention is applicable to dicotyledonous and monocotyledonous species and is readily applicable to new and/or improved transformation techniques. For efficient production of transgenic plants from plant cells or plant tissue, it is desirable that the plant tissue used for transformation possess a high capacity for regeneration. Techniques are known in the art to regenerate plants from transformed plant tissue cultures of plant cells.

The transgenic plants produced in accordance with this invention may, as previously stated, be any dicotyledonous or monocotyledonous species and are preferably from useful species such as maize (corn), peas, soybean, alfalfa, cassava, potato, cotton, and cereals (e.g., barley, oats, rye, triticale and wheat). Corn refers to *Zea Mays* and all species and varieties that can be bred with it. Wheat refers to all of *Triticum aestivum* varieties including but not limited to spring, winter, and all facultative wheat varieties. Wheat includes any other wheat species, including but not limited to durum wheat (*Triticum durum*), spelt (*Triticum spelta*), emmer (*Triticum dicoccum*), and wild wheat (*Triticum monococcum*). Wheat also includes any species that can be bred with any of the aforementioned wheat species. Soybeans refers to *Glycine max* and any species or variety that can be bred with it. Rice refers to *Oryza sativa* and any species or variety that can be bred with it. Barley refers to *Hordeum vulgare* and any species or variety that can be bred with it. Oats refers to *Avena sativa* and any species or variety that can be bred with it. Canola is a coined name recently given to seed, oil, and meal produced by genetically modified rapeseed plants, oilseed rape (*Brassica napus* L.) and turnip rape (*B. campestris* L), herein canola includes all rapeseed plants and organisms that can be bred with them. *Agrobacterium tumefaciens* as used herein includes all strains and types of this species. Cotton refers to all plants in the genus *Gossypium* and all plants that can be bred with them.

A method according to the invention comprises introducing a DNA molecule containing a promoter functional in plant cells operably linked to a nucleic acid sequence encoding a heat-stable NB-LRR polypeptide (exemplary isolated DNA molecules are described in FIGS. 8, 9, 10, and 11), and producing a plant (as well as fertile progeny plant of such a plant) from the transformed plant cell. Progeny includes fertile descendants of a particular plant or plant line.

The invention further relates to the production of transgenic seed. "Transgenic seed" means a plant seed whose nucleus has been altered by the incorporation substantially pure nucleic acid molecule encoding a polypeptide comprising a NB-LRR that confers a heat-stable defense response; for example a NB-LRR polypeptide that includes a domain which includes a heat-stable subdomain of the LRR, the polypeptide modulating a defense response in a plant expressing such polypeptide, e.g., by transformation as described herein. The term "transgenic plant" is used to refer to the plant produced from an original transformation event, or progeny from later generations or crosses of a plant to a transformed plant, so long as the progeny contains a nucleus with the recombinant DNA in its genome.

The invention further relates to a transgenic plant component. By "plant component" is meant a part, segment, or organ obtained from an intact plant or plant cell. Exemplary plant components include, without limitation, somatic embryos, leaves, stems, roots, flowers, tendrils, fruits, scions, seeds, tubers, and rootstocks.

Other features and advantages of the invention will be apparent from the following Drawings, Detailed Description, and the Claims.

BRIEF DESCRIPTION OF THE DRAWINGS

FIG. 1A shows the dwarf phenotype of snc1-1 at 22° C. is suppressed by a higher temperature of 28° C. Shown are 4-week-old plants.

FIG. 1B shows the int102 mutation enables snc1-1 to retain resistance to a virulent pathogen at 28° C. Shown is the growth of *Pseudomonas syringae* pv tomato (Pst) DC3000 in the wild type, snc1-1, and int102-1 snc1-1 at 22° C. and 28° C.

FIG. 1C shows the int102 mutation confers a dwarf phenotype to snc1-1 at 28° C. Shown are 3-week-old plants.

FIG. 1D shows that the expression of defense genes is upregulated in int102-1 snc1-1 at both 22° C. and 28° C. and this upregulation in int102-1 snc1-1 is dependent on PAD4. Expression of PR1 and SNC1 is analyzed by RNA blot.

FIG. 1E shows the dwarf phenotype of int102-1 snc1-1 at 28° C. is suppressed by pad4 and nahG. Shown are wild type, int102-1 snc1-1pad4, and int102-1 snc1-1 nahG grown at 28° C. after bolting.

FIG. 2A shows that the hypersensitive response (HR) is induced by SNC1 with the snc1-3 mutation at 28° C. Four p35S::SNC1:GFP constructs: SNC1 wild-type (WT), SNC1-1, SNC1-3 and SNC1-4 (containing both snc1-1 and snc1-3 mutations), were infiltrated via *Agrobaterium* (agro-infiltrated) into *Nicotiana benthamiana* (Nb) leaves. Shown are leaves at 3 days after infiltration. HR is indicated by arrows.

FIG. 2B shows the subcellular localization of the SNC1: GFP proteins in Nb at 22° C. and 28° C. Infiltrated leaves as described in FIG. 2A were analyzed by fluorescent microscopy one day before the onset of HR. SNC1-3 and SNC1-4 but not SNC1-1 were retained in the nucleus at 28° C. SNC1WT had a weaker signal and a longer exposure time was used to take the image.

FIG. 2C shows the subcellular localization of the SNC1: GFP proteins in *Arabidopsis thaliana* protoplasts. The same set of four constructs as in FIG. 2A were transformed into *Arabidopsis* protoplasts and the GFP signals were observed at 12 hours after transformation by fluorescent microscopy. SNC1WT was exposed for a longer time than the other three samples.

Abbreviations: WT, SNC1WT:GFP; -1, SNC1-1:GFP; -3, SNC1-3:GFP; -4, SNC1-4:GFP; -3:NES, SNC1-3:GFP: NES; -4:NES, SNC1-4:GFP:NES.

Figure 3:
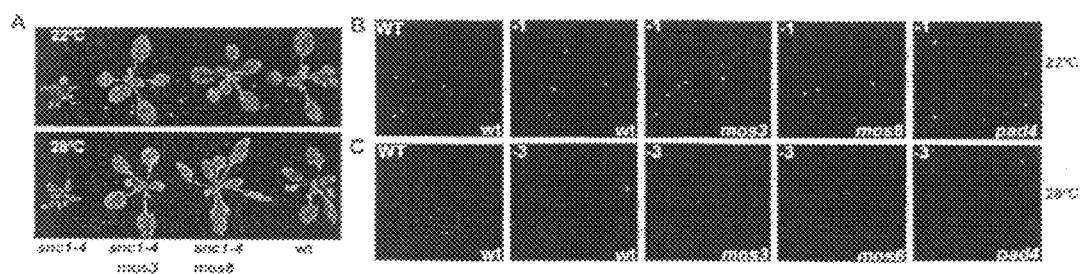

FIG. 3A-3C show that the MOS3 and MOS6 genes are required for the SNC1-3 protein activity.

FIG. 3A shows that the dwarf phenotype of snc1-4 is suppressed by mos3 or mos6. Shown are 3-week-old seedlings of the wild type, snc1-4 mos3, snc1-4 mos6, and snc1-4 at 22° C. and 28° C.

Figure 2:
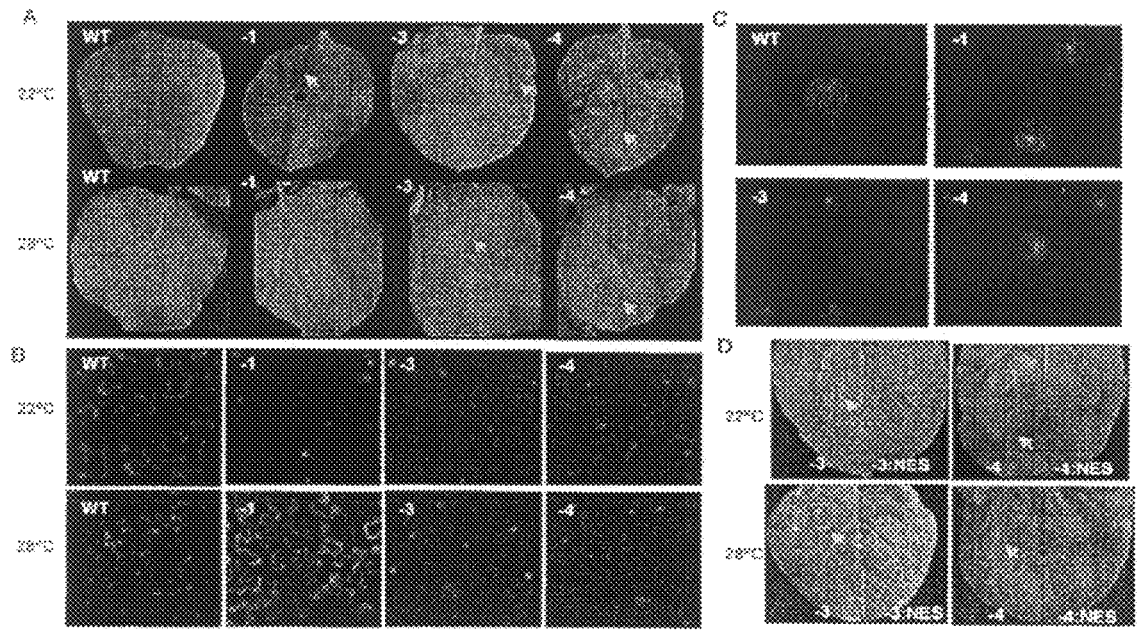
FIGS. 2A-2C show that the snc1-3 mutation confers temperature-insensitive activity to SNC1.
FIG. 2D shows a nucleus export signal (NES) abolishes the activities of SNC1-3 and SNC1-4. SNC1-3:GFP, SNC1-3: GFP:NES, SNC1-4:GFP, and SNC1-4:GFP:NES were agro-infiltrated in Nb and their HR inducing activities were assayed at 22° C. and 28° C. The left half of each leaf was infiltrated with the SNC1:GFP fusion, and the right half of the leaf was infiltrated with the corresponding SNC1:GFP fusion with NES. Shown are leaves at 3 days after infiltration. HR indicated by arrows was only observed with fusion proteins without NES.

FIGS. 3B and 3C show the subcellular localization of the SNC1-1:GFP protein at 22° C. (FIG. 3A) and SNC1-3:GFP at 28° C. (FIG. 3C) in wild-type (wt), mos3, mos6, and pad4 plants. SNC1WT:GFP, SNC1-1:GFP, and SNC1-3:GFP were expressed at 22° C. or 28° C. in protoplasts isolated from the mos3, mos6, and pad4 mutant plants and the GFP signals were observed at 12 hours after transformation by fluorescent microscopy. The SNC1-1 and SNC1-3 proteins were present in the nucleus in the pad4 mutant as in the wild type, but were mostly in the cytosol and plasma membrane in mos3 and mos6. Abbreviations: wt, wild type; others are the same as in FIG. 2.

Figure 4:
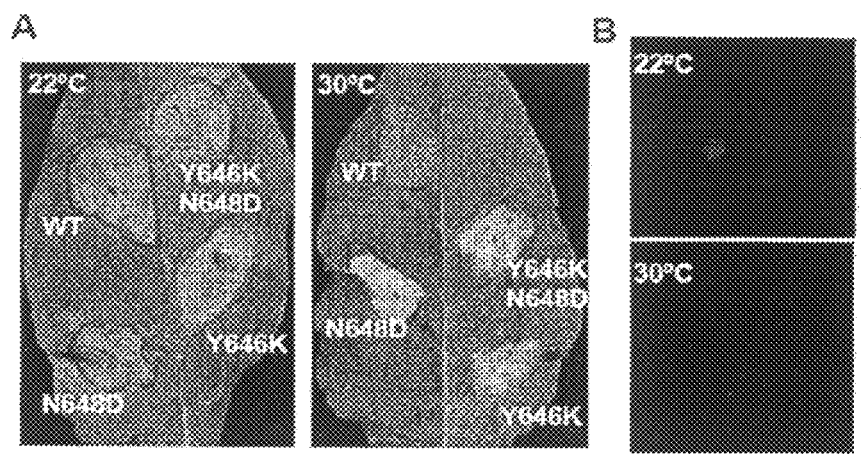

FIGS. 4A-4B show that the mutations in the N gene confer temperature-insensitive defense responses.

FIG. 4A shows HR induced by the WT and three mutant N genes at 22° C. and 30° C. in Nt. The WT and mutant N genes were agro-infiltrated in Nt together with its elicitor p50. The WT N gene induced HR at 22° C. but not 30° C., while the Y646K, and Y646KN648D mutants induced HR at both temperatures.

FIG. 4B shows the localization of N-citrine in Nb at 22° C. and 30° C. when co-expressed with p50. The N-citrine chimeric gene was agro-infiltrated in Nb with p50, and the citrine signal was monitored up to three days. The nuclear localization of the N-citrine protein was observed at 22° C. but not at 30° C.

Figure 5:
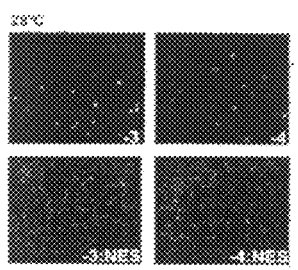

FIG. 5 shows that the nucleus export signal (NES) suppresses the nuclear localization of the SNC1-3 and SNC1-4 proteins. Shown are the localization of SNC1-3:GFP, SNC1-4:GFP, SNC1-3:GFP:NES, and SNC1-4:GFP:NES proteins expressed in Nb at 28° C. While SNC1-3:GFP and SNC1-4:GFP were mostly localized to the nucleus, SNC1-3:GFP:NES and SNC1-4:GFP:NES had reduced expression in the nucleus and are also found in the cytosol and the plasma membrane. Abbreviations are the same as in FIG. 2.

Figure 6:
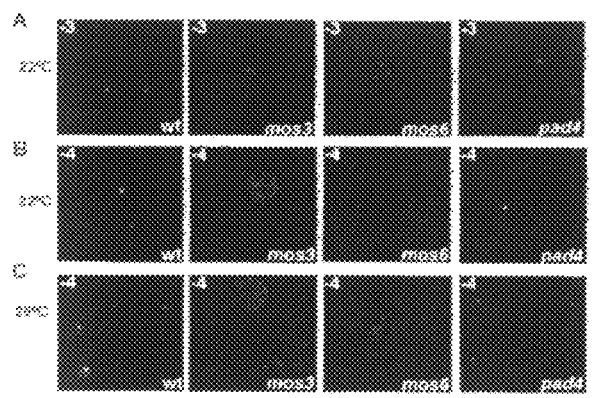

FIG. 6 shows that the MOS3 and MOS6 genes are required for the SNC1-3 and SNC1-4 activities. Subcellular localization of SNC1-3:GFP at 22° C. (A) and SNC1-4:GFP proteins at 22° C. (B) and 28° C. (C) in wild type (wt), mos3, mos6, and pad4. SNC1-3:GFP, and SNC1-4:GFP were expressed at 22° C. and 28° C. in protoplasts isolated from the mos3, mos6, and pad4 mutant plants, and the GFP signals were observed at 12 hours after transformation by fluorescent microscopy. The SNC1-3 and SNC1-4 proteins were present in the nucleus in the pad4 mutant as in the wild type, but were mostly in the cytosol and plasma membrane in mos3 and mos6 at both temperatures. Abbreviations: wt, wild type; others are the same as in FIG. 2.

FIG. 7 shows the amino acid sequences of SNC1 proteins. The TIR, NB-ARC, and LRR domains are spectively presented in italics, Bold, and double-underline. Mutations of snc1-1, snc1-3, and snc1-5 are highlighted.

FIGS. 8A and 8B show a list of 500 homologous sequences of SNC1 found in *Arabidopsis thaliana*. Genbank accession numbers are shown.

FIGS. 9A, 9B, and 9C show a list of SNC1 homologs in species other than *Arabidopsis*. A list of 500 homologous sequences of SNC1 found in non-*Arabidopsis thaliana* species. Genbank accession numbers are shown.

FIG. 10 shows R mutations useful for conferring heat-stable disease resistance. A list of mutations in select R proteins useful for conferring heat-stable disease resistance is shown.

FIG. 11 shows an alignment of R genes and modifications to render R genes useful for conferring a heat-stable defense response in select plants.

DETAILED DESCRIPTION

Overview

The plant immune system consists of multiple layers of responses to various biotic attacks, enabling a success in plant survival, fitness and reproduction (1, 2). These defense responses are modulated by abiotic environmental factors such as light, humidity, and temperature (3-7). As is mentioned above, a high temperature suppresses a number of plant defense responses rendering a normally resistant plant susceptible to pathogen attacks. This temperature sensitivity poses a challenge to agriculture and yet the molecular mechanisms underlying this temperature modulation are unknown. Below it is demonstrated that the disease resistance (R) gene known to recognize pathogen effectors (8, 9) is a temperature sensor conferring temperature sensitivity in disease resistance. Further, specific residue alterations in the SNC1 and the N proteins counteract this temperature effect and sustain defense responses at high temperatures. These findings are useful to generate effective plant immune responses within a broader temperature range.

As is discussed in greater detail below, an *Arabidopsis thaliana* mutant snc1-1 was used as a starting strain to isolate mutants that retain enhanced disease resistance at higher temperatures. snc1-1 has a missense mutation in the NB-LRR type of R protein SNC1, as well as a constitutive defense response and a dwarf phenotype at normal growth temperature 22° C. but is disease susceptible with a normal growth phenotype at a higher temperature such as 28° C. This mutant screen yielded mutants with a snc1-1 dependent growth and defense mutant phenotype at both 22° C. and 28° C. One mutant identified from this screen was cloned as a new allele (snc1-4) of SNC1 with an E640 mutated to K (referred as the snc1-3 mutation) in the SNC1 protein (Table 1). This snc1-3 mutation alone is sufficient to induce enhanced disease resistance at both low and high temperatures without the original snc1-1 mutation. This finding revealed for the first time that an alteration in the R protein rather than other players in plant innate immunity is sufficient to confer temperature insensitivity. Thus, the R gene is a temperature sensor in defense responses. In addition, specific mutations in the R proteins SNC1 alter temperature sensitivity, making them active at both low and high temperatures.

The molecular basis for this temperature sensitivity in SNC1 was also examined. Temperature was found to influence the subcellular localization of the SNC1 protein: the nuclear localization of SNC1 correlated with its biological activity. The SNC1-1 protein that is active only at 22° C. is concentrated in the nucleus at 22° C. but is out of the nucleus at 28° C. while the SNC1-3 protein that is active at both 22° C. and 28° C. stays in the nucleus at both temperatures. The addition of a nucleus export signal to the SNC1-3 protein resulted in exclusion of the SNC1-3 protein from the nucleus, leading to a loss of SNC1 activity at 28° C. Thus, temperature modulation of R protein localization is the basis for temperature sensitivity of R proteins and consequently temperature sensitivity of disease resistance.

These findings in the *Arabidopsis* SNC1 have a general application for disease resistance mediated by other NB-LRR R proteins. For example, the tobacco N gene (11) mediates resistance to cauliflower mosaic virus, and this resistance is suppressed by a higher temperature of 30° C. Cognate mutations of snc1-3 when introduced into the N gene enable a heat-stable resistance (Table 1), indicating a universal mechanism in temperature sensitivity of disease resistance. Although the molecular consequences induced by these mutations are not well understood, it is believed that a change of the charges from negative to positive around the E640 residue in the LRR region alters the conformation of the R protein or its interaction with other proteins. By mutating E640 to R in SNC1 a heat-stable HR (Table 1) was obtained, supporting this hypothesis.

The details of the aforementioned experiments now follow.

Experimental

Figure 1:
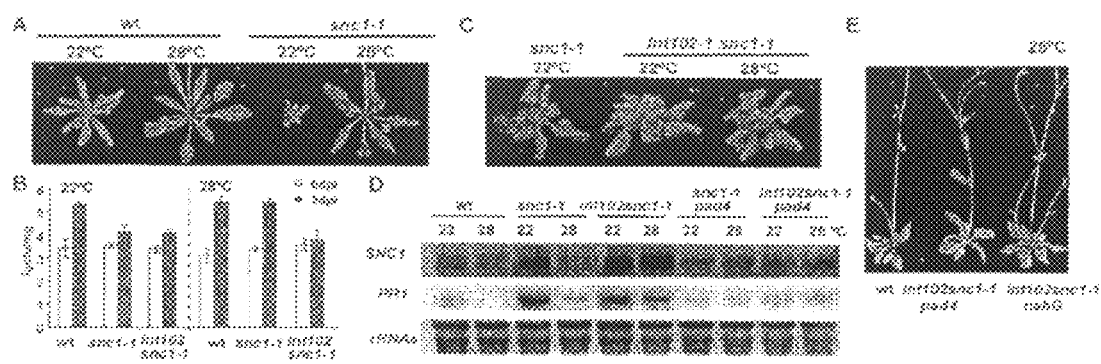
FIGS. 1A-1E show that the int102 mutant has a temperature-insensitive defense response.

A genetic screen in snc1-1 (10) for mutants defective in high temperature suppression of defense responses was carried out. The wild-type Arabidopsis plants do not have constitutive defense responses as these responses usually compromise plant growth and sometimes cause cell death. The Arabidopsis snc1-1 mutant has a constitutive defense response and a dwarf phenotype under normal growth temperature 22° C. due to a missense mutation in the linker region of SNC1(10), and both phenotypes are suppressed by a higher growth temperature such as 28° C. (7) (FIG. 1A, B). One such mutant isolated, int (insensitive to temperature)102-1, has a snc1-1 dependent dwarf phenotype at both 22° C. and 28° C. (FIG. 1C). The int102-1snc1-1 mutant is as resistant to Pseudomonas Syringae pv. tomato (Pst) DC3000 as snc1-1 at 22° C., but retains resistance at 28° C. in contrast to snc1-1 (FIG. 1B). Therefore, the int102-1snc1-1 mutant indeed has a temperature-insensitive (heat-stable) constitutive defense response. Consistently, the expressions of PR1 and SNC1, two genes responsive to an increase of salicylic acid (SA) associated with enhanced disease resistance (7, 12), were higher in int102-1snc1-1 than in the wild type or snc1-1 at 28° C. (FIG. 1D). Both the defense and the growth phenotypes of int102-1snc1-1 can be suppressed by nahG (13) coding a SA degradation enzyme and by pad4 (14) defective in defense responses (FIG. 1D, E, and data not shown), further demonstrating an upregulation of defense responses in the int102-1snc1-1 mutant at 28° C.

We cloned the INT102 gene based on its tight linkage to SNC1 in a mapping population (online methods). Sequencing the SNC1 gene in int102-1snc1-1 revealed a G to A point mutation causing a change of glutamic acid to lysine (named as snc1-3) at amino acid residue 640 in the LRR domain of SNC1 (Table 1).

TABLE 1

Mutations isolated or generated in the SNC1 and the N proteins.

| Genes | starting residue # | Sequences | HR at high temperatures |
|---|---|---|---|
| SNC1 WT | 639 | EELD | no (SEQ ID NO: 2) |
| SNC1-3 | | EKLD | yes (SEQ ID NO: 3) |
| SNC1 E640R | | ERLD | yes (SEQ ID NO: 4) |
| N WT | 637 | EYVN | no (SEQ ID NO: 5) |
| N Y646K | | EKVN | yes, weak (SEQ ID NO: 6) |
| N N648D | | EYVD | yes (SEQ ID NO: 7) |
| N Y646K N648D | | EKVD | yes (SEQ ID NO: 8) |

Shown are the aligned regions of SNC1 and N proteins with mutated residues underlines. The wild-type and the mutant genes were tested for HR-inducing activities at 28° C. (for SNC1) and 30° C. (for N).

The int102-1snc1-1 mutant is therefore named snc1-4, and it contains both the snc1-1 and snc1-3 mutations. To confirm that the snc1-3 mutation is responsible for the temperature-insensitive disease resistance phenotype, we generated transgenic plants carrying the genomic fragments of either the wild-type or the mutant SNC1-4 genes in the wild-type Col-0 plants. However, transgenic plants carrying the wild-type SNC1 gene exhibited a dwarf phenotype similar to those carrying the SNC1-4 mutant gene (data not shown), and this auto-activation of the SNC1 as a transgene is likely due to a loss of transcriptional repression imposed at its endogenous chromosomal location (15). We subsequently developed a transient assay for the SNC1 gene activity in Nicotiana benthamiana (Nb) by the hypersensitive response (HR), a form of programmed cell death induced by the activation of R proteins. The SNC1 protein was tagged by the green fluorescent protein (GFP) at the carboxyl-terminus and expressed under the strong CaMV 35S promoter. This p35S::SNC1:GFP fusion gene was expressed in Nb leaves by Agrobacterium-mediated infiltration (agro-infiltration), and HR symptoms such as collapsed leaves were monitored at 22° C. and 28° C. respectively over a period of 3 days after infiltration. In contrast to the wild-type SNC1 (SNC1WT) gene that did not cause any HR, the SNC1-1 mutant gene induced HR at 22° C. but not at 28° C. while the SNC1-3 and SNC1-4 genes each induced HR at both temperatures (FIG. 2A). Thus, snc1-3 is indeed the mutation responsible for the int102-1snc1-1 phenotype. Furthermore, the snc1-3 mutation alone (without snc1-1) is sufficient to induce temperature-insensitive defense responses. This result indicates that temperature sensitivity of disease resistance is controlled by the R gene rather than other regulatory components and that a mutation in an NB-LRR type of R gene is sufficient to confer temperature-insensitive disease resistance.

To further investigate the mechanism underlying temperature sensitivity of defense responses, we carried out a suppressor screen in the heat-stable snc1-4 mutant background. Mutants that regained high-temperature inhibition of defense responses were isolated and named rit (revertant of int). One such mutant rit1snc1-4 had a snc1-1 like phenotype: dwarf at 22° C. but wild-type like at 28° C. suggesting a regaining of temperature sensitivity. Correlated with the growth defect, the rit1snc1-4 has enhanced disease resistance to virulent pathogen Pst DC3000 at 22° C. and this elevated defense is suppressed at 28° C. At 22° C., Pst DC3000 had a similar growth reduction in rit1snc1-4 as in snc1-1 and snc1-4 compared to the wild-type Col. At 28° C., snc1-4 exhibited an inhibition of bacterial growth to a similar extent as at 22° C. In contrast, rit1 snc1-4 lost the inhibition of bacterial growth at 28° C. and supported bacterial growth to a similar extent as snc1-1 and the wild type. Therefore rit1 indeed reverses the heat-stable resistance phenotype to the heat-sensitive phenotype.

We found that rit1 is an intragenic suppressor of snc1-4. There is no phenotypic segregation in the F2 progenies of a cross of rit1 snc1-4 with wild-type Col or Ler grown at 28° C. indicating that the rit1 is very closely linked to the SNC1 gene. Sequencing the entire SNC1 genomic fragment in the rit1 snc1-4 mutant identified a G to A point mutation resulting in a serine substitution of glycine at amino acid residue 380 (FIG. 7). We named this G380S mutation snc1-5 and this new allele with snc1-1, snc1-3, and snc1-5 mutations as snc1-6 (FIG. 3C). This glycine residue resides immediately after the putative GxP or GLPL motif in the NB-ARC domain. This motif was previously identified as important for nucleotide binding and mutations in residues close to the motif might compromise activation of NB-LRR proteins (30).

A second intragenic suppressor named rit4 was identified from the same rit screen. This mutant was independent of rit1 as it was isolated from a different mutagenesis pool and had an additional phenotype unrelated to defense. Interestingly, we found the same G to A alteration resulting in a G380S mutation as in rit4. That two independent but identical mutations result in the same rit phenotype confirms that snc1-5 is indeed the mutation responsible for reverting the temperature insensitivity of snc1-4.

This conclusion is further supported by the SNC1-6 activity in the Nb transient expression system. The snc1-5 mutation was introduced into the p35S::SNC1-4:GFP construct to create p35S::SNC1-6:GFP. While SNC1-4 induced HR in Nb at both 22° C. and 28° C., SNC1-6 induced HR only at 22° C. but not at 28° C. Thus snc1-5 mutation appears to be a suppressor of the heat-stable SNC1-4 activity specifically at 28° C. and it does not significantly suppress SNC1-4 activity at 22° C. This notion is further supported by the failure of inhibiting the SNC1-1 22 C activity with the snc1-5 mutation at 22° C. (data not shown).

With the identification of different forms of SNC1 conferring defense responses of different temperature sensitivity, we conclude that the NB-LRR gene SNC1 is the temperature sensitive component causing temperature sensitivity of the whole defense responses it induces. An elevated temperature inhibits plant immunity probably through the very early component of the signaling pathways that is the NB-LRR genes.

We further investigated the molecular basis underlying the temperature sensitivity of the NB-LRR type of R gene SNC1. A correlation was observed between the nuclear localization of the SNC1 protein and its HR-inducing activity in Nb at both temperatures. A very weak GFP signal was detected in the cytosol and the plasma membrane for the SNC1WT:GFP fusion protein (FIG. 2B). The SNC1-1:GFP mutant fusion protein was localized to the nucleus at 22° C. (FIG. 2B), confirmed by nucleus staining with 4',6-diamidino-2-phenylindole (DAPI) (data not shown), but it was found in the cytosol and the plasma membrane at 28° C. (FIG. 2B). In contrast, both SNC1-3:GFP and SNC1-4:GFP were localized to the nucleus at both 22° C. and 28° C. (FIG. 2B). The localization of these SNC1 proteins was confirmed in a transient expression system in *Arabidopsis thaliana*. When expressed at 22° C. in *Arabidopsis* protoplasts, SNC1-1:GFP, SNC1-3:GFP, and SNC1-4:GFP, but not SNC1WT:GFP, were localized predominantly in the nucleus (FIG. 2C). At 28° C., only SNC1-3:GFP and SNC1-4:GFP, but not SNC1WT:GFP or SNC1-1:GFP, were found in the nucleus (FIG. 3B, 3C, FIG. 6). It appears that temperature influences the localization of the SNC1 protein and the snc1-3 mutation causes a nuclear localization of SNC1 even at a higher temperature.

To determine whether the nuclear localization of SNC1 is the cause or the consequence of the enhanced defense responses at elevated temperatures, we added a nucleus export signal (NES) (16) to the SNC1:GFP fusions and expressed these constructs in Nb leaves. The addition of NES largely reduced the nuclear localization of SNC1-3:GFP and SNC1-4:GFP at 28° C., resulting in their expression in cytosol and plasma membrane as well (FIG. 5). Neither SNC1-3: GFP:NES nor SNC1-4:GFP:NES induced HR in Nb leaves, in contrast to SNC1-3:GFP and SNC1-4:GFP (FIG. 2D). Thus, nuclear localization is critical for the mutant SNC1 proteins to induce defense responses at a higher temperature. This finding is consistent with the emerging finding that nuclear localization of some R proteins is essential for them to confer disease resistance (17, 18).

Nuclear-cytosyl partition of proteins has critical roles for diverse plant developmental signaling and environmental responses, and a few genes involved in the nuclear-cytosyl shuttling processes are shown to be required for defense responses (19, 20). For instance, mutations in MOS3 (encoding a putative nucleoporin Nup96) or MOS6 (encoding a putative importin α3) could suppress enhanced disease resistance in snc1-1 (21, 22), although the exact mechanisms are not well understood. We tested whether genes involved in nuclear-cytosol transport are essential for defense responses induced by the SNC1 mutant protein at high temperatures. The mos3 and mos6 mutations were each introduced into the snc1-4 mutant, and both the snc1-4 mos3 and the snc1-4 mos6 double mutants exhibited a wild-type growth phenotype at 22° C. and 28° C. (FIG. 3A), indicating a requirement of functional MOS3 and MOS6 for the SNC1-4 activities at both temperatures. To determine whether MOS3 and MOS6 regulate SNC1-mediated defense response through SNC1 localization, we expressed different forms of p35S::SNC1:GFP in protoplasts isolated from the wild-type, mos3, and mos6 plants. The nuclear localization of SNC1-1 at 22° C. in the wild type was largely suppressed by the mos3 and mos6 mutations (FIG. 3B), indicating that MOS3 and MOS6 likely regulate snc1-1 mediated defense through the localization of the SNC1-1 protein. Similarly, nuclear localization of the SNC1-3 and SNC1-4 proteins at 22° C. and 28° C. in the wild type were greatly reduced in the mos3 and mos6 mutants, and the SNC1-3 and SNC1-4 proteins had enhanced cytosol and plasma membrane localization in the two mutants (FIG. 3C, and FIG. 6). Thus, the activities of SNC1-3 and SNC1-4 at a high temperature requires the two genes involved in nuclear-cytosyl transport. In contrast to the mos3 and mos6 mutations, the loss-of-function mutation of PAD4 that functions downstream of R protein activation did not alter the nuclear localization of the SNC1 mutant proteins although it suppresses the snc1 mutant phenotype similarly to mos3 and mos6 (FIG. 1E, 3B, 3C, and FIG. 6). These data indicate that MOS3 and MOS6 mediate SNC1-induced defense responses via regulating the R protein SNC1. It further demonstrates that nuclear localization of the SNC1 protein at high temperature is the cause rather than the consequence of heat-stable defense responses.

To determine whether the finding on temperature sensitivity in defense responses induced by the *Arabidopsis* SNC1 is a general phenomenon for disease resistance, we introduced similar mutations of snc1-3 (SEQ ID NO: 1) to a tobacco R gene N that confers resistance to tobacco mosaic virus (TMV). It is well known but not understood how the N-containing plants lose resistance at a higher temperature of 30° C. (11). We altered two residues in the N protein by site-directed mutagenesis: one is the Y646K mutation corresponding to the snc1-3 mutation (E640K) of SNC1 and the other is the N640D mutation corresponding to D642 of SNC1 (Table 1). When co-expressed with its elicitor p50 in *Nicotiana tabacum* (Nb) by agro-infiltration, the wild-type N gene triggered HR at 22° C. but not at 30° C. (FIG. 4A, Table 1). In contrast, the three mutant N genes with Y646K, N648D, or Y646K N648D mutations induced HR in Nb at both 22° C. and 30° C. together with the N elicitor p50 (FIG. 4A, Table 1). These mutations do not appear to confer constitutive auto-activities because they did not cause HR in the absence of p50 (data not shown). Thus, the N gene is responsible for the temperature sensitivity of TMV resistance, indicating that other NB-LRR type of R genes function as temperature sensors in disease resistance and that temperature sensitivity can be altered by specific mutations in the R proteins to make heat-stable disease resistance.

We determined whether temperature sensitivity of the N gene is correlated with the N protein localization similar to that of the SNC1 gene. When expressed together with p50 in *N. benthamiana*, the N-citrine fusion protein was localized to the nucleus at 22° C. (FIG. 4B), consistent with previous findings (18). However, no signal could be detected in the nucleus when plants were incubated at 30° C. (FIG. 4B). This indicates that nuclear localization of activated wild-type R protein(s) is subject to temperature modulation, similarly to that of the active form of the mutant R protein such as SNC1-1.

The molecular basis of temperature-insensitive mutants of R proteins is not totally understood. This is not merely due to an over-activation of R proteins because the SNC1-1 mutant protein apparently has the same activity as SNC1-4 at 22° C. and yet has no activity at 28° C. The E640K mutation in SNC1 can potentially induce local post-translational protein modification such as ubiquitination, sumoylation, acetylation, and biotylation. Especially the 'EKID' sequence around snc1-3 and intriguingly the 'LKIG' sequences around snc1-1 are predicted to be sumoylation sites by sumoplot login. However, the N648D alone in N without the Y646K mutation is sufficient to induce HR at high temperatures, indicating that sumoylation is not the basis or the only basis for the activity. We therefore tested whether a charge change rather than a local protein modification is responsible for temperature insensitivity by introducing an E640R mutation to SNC1 (Table 1). Similar to SNC1-3:GFP, SNC1E640R:GFP induced HR at 28° C. and was localized to the nucleus when expressed in Nb (data not shown). Both E to K and E to R mutations add positive charges to the region and could potentially generate a local nuclear localization signal (23). To test whether these mutations generate such a signal or are sufficient to induce nuclear localization, we created shorter versions of the SNC1:GFP proteins consisting of the linker region and the LRR domain of the SNC1 protein. Neither the snc1-3 nor the snc1-1 mutations conferred a nuclear localization to the shorter SNC1:GFP fusion proteins (data not shown), indicating that these mutations do not function autonomously to induce SNC1 nuclear localization.

The R protein activation involves alteration of intra-molecular interactions, with opening of the NB domain and possibly allowing interaction of the amino-terminal domain with downstream signaling molecules (24, 25). It is possible that a high temperature can influence the intra-molecular interactions and keep the R protein in an inactive closed form. A protein 3-D structure modeling suggested that the SNC1 E640 and a few nearby residues including D642 could form a more negatively charged pocket and this pocket might have a direct contact with positively charged residue(s) in the ARC domain. The E640K/R mutations could disrupt the interaction between the LRR domain and the ARC domain, leading to an active conformation of the SNC1 protein at a high temperature. Alternatively, these mutations could alter the interaction of SNC1 with downstream signaling molecules, leading to an active signaling event at high temperatures.

The above-described experimental results were obtained using the following materials and according to the following methods.

Material and Methods

The *Arabidopsis thaliana* plants were grown on soil at 22° C. or 28° C. under constant light for morphological phenotypic analysis, and under a photoperiod of 12 hour (hr) light/12 hr dark for disease resistance test. *Arabidopsis* seedlings used for protoplast transformation were grown on solid medium under a photoperiod of 8 hr light/16 hr dark. The *Nicotiana tabacu* (Nt) and *Nicotiana bethamiana* (Nb) plants were grown in the greenhouse. For chemical mutagenesis, the snc1-1 seeds were treated with 0.25% EMS (ethane methyl sulfonate) for 12 hours. For cloning the INT102 gene, the int102-1snc1-1 mutant in Col-0 was crossed to the Ws-2 wild type and standard mapping method (26) was used to identify the intervals containing the INT102 gene. The p35S::SNC1: GFP construct consists of the strong 35S CaMV promoter, the genomic fragment of the SNC1 coding region (from the translation start site to the last amino acid), and the green fluorescent protein (GFP) fused in frame to the carboxyl-terminus of SNC1. Site-directed mutagenesis was carried out with 'QuikChange' kit according to manufacture's instruction (Stratagene). The *Arabidopsis* protoplasts were generated from plate-grown seedlings according to methods by Zhai and Vatamaniuk (in press). RNA blot analysis, pathogen resistance test, and transient expression in Nb and Nt was performed as described (7, 27, 28).

Plant material and growth condition. The *Arabidopsis thaliana* plants were grown on soil at 22° C. or 28° C. under constant light with a relative humidity between 40% and 60% for morphological phenotypic and gene expression analysis. *Arabidopsis* seedlings used for protoplast transformation were grown on solid medium with 1/2 MS salts, 2% sucrose, and 0.8% agar and under a photoperiod of 8 hr light/16 hr dark. *Nicotiana tabacum* (Nt) and *Nicotiana bethamiana* (Nb) plants were grown in the greenhouse.

Mutant screen. The snc1-1 seeds were treated with 0.25% EMS (ethane methyl sulfonate) for 12 hours. Approximately 40,000 M2 plants (derived from 4,000 M1) were screened at 28° C. for the snc1-1 like dwarf phenotype. Putative mutants were then crossed to the wild-type Col-0, and the $F_2$ population was analyzed to determine whether they are snc1-1 dependent or not.

Map-based cloning. The mapping population was created by crossing the int102-1 mutant in the Col-0 accession to the wild type of the Ws-2 accession. Dwarf plants among the $F_2$ progenies grown at 28° C. were chosen for mapping. Bulked segregation analysis was preformed on pools of 40 plants with SSLP, CAPS, and dCAPS markers between Col-0 and Ws-2 (26). The INT102 gene was found to be linked to marker VRN2 that is 1 cM from the SNC1 gene. Further analysis of 240 dwarf plants revealed no recombination between INT102 and SNC1, indicating a tight linkage of the two genes.

Generation of constructs. A 5.5 kb fragment containing the SNC1 coding region and the 3'UTR was isolated from the BAC clone F5D3 from ABRC. A BamHI restriction site was added to this genomic fragment before the stop codon of SNC1 via polymerase chain reaction (PCR). The NcoI-BamHI fragment containing the SNC1 coding region without the stop codon was inserted into pSAT-N1 vector (29) to generate the p35S::SNC1:GFP construct. The SNC1-1, SNC1-3, and SNC1-4 mutations were introduced into p35S::SNC1:GFP through site-directed mutagenesis with the 'QuikChange' kit according to manufacture's instruction (Stratagene). The cassettes of various p35S::SNC1:GFP were excised at the PI-PspI sites and cloned into the pHPT binary vector (29) to generate pHPT-SNC1, pHPT-SNC1-1, pHPT-SNC1-3, and pHPT-SNC1-4 constructs.

Transient expression in Nb and Nt. Each of these above binary vectors was then transformed into *Agrobacterium tumefaciens* stain C58C1 (30). Cultures of the transformed *A. tumefaciens* were grown overnight to $OD_{600}$ of 1.0 in liquid LB. Cells were then collected by centrifugation and resuspended in the induction medium (10 mM MES, pH5.7, 10 mM $MgCl_2$, 200 µM acetosyringone) to $OD_{600}$ of 0.5. After sitting at room temperature for 3 hrs, the Agrobacterial cells were infiltrated into the abaxial surface of Nb or Nt leaves using 1 ml needleless syringes. Infiltrated plants were subsequently incubated at 22° C. or 28° C. before infiltrated leaves were examined for GFP signals under a microscope (model BX61, Olympus) within a 48 hr period after inoculation.

RNA analysis. Total RNAs were extracted using Tri Reagent (Molecular Research, Cincinnati, Ohio) from leaves of 3-week-old plants. Twenty micrograms of total RNAs per sample were used for RNA gel blot analysis.

Pathogen resistance assay. *P. syringae* pv. tomato DC3000 was grown overnight in the KB medium and resuspended at $10^8$ ml in a solution of 10 mM $MgCl_2$ and 0.02% Silwet L-77. Two-week-old seedlings were dip inoculated with bacteria and kept covered for 1 h. The amount of bacteria in plants was analyzed at 1 h after dipping (day 0) and 3 days after dipping (day 3). The aerial parts of three inoculated seedlings were pooled for each sample and three samples were collected for each genotype at one time point. Seedlings were ground in 1 ml of 10 mM $MgCl_2$ and serial dilutions of ground tissue were used to determine the number of cfu per miligram of leaf tissues.

Engineering Heat-Stable Disease Resistance

As is discussed above, the invention involves engineering heat-stable disease resistance in plants where a heat-labile race-specific disease resistance is normally found. In general, mutant forms of an NB-LRR type of R protein that are responsible for this race-specific resistance are generated. Alternatively, mutant forms in natural populations are identified and isolated according to standard methods, followed by introducing such isolated R variants into plants, rendering such plants disease resistant against one or more pathogens at a temperature which would typically mask such a defense response.

Such R variants are useful to modify temperature sensitivity in disease resistance. Furthermore, R proteins may be altered at specific sites to generate an R protein which not only mediates disease resistance but one that is also heat-stable rendering a plant resistant to disease above its heat masking temperature.

As is also discussed above, the invention features methods for conferring disease resistance to a plant at a temperature at which such a disease response is suppressed, thereby attenuating heat masking. Such methods include, without limitation, overexpression or ectopic expression a heat-stable NB-LRR disease resistance polypeptide (such as SNC1-3, SNC1 E640R, N Y646K, N648D or N Y738K N648D or any polypeptide described in FIG. 9 and FIG. 10).

To test the ability of a construct described herein to confer disease resistance to a pathogen, transgenic plants expressing such construct are planted and disease resistance is compared to non-transformed plants using techniques familiar to those of skill in the art at masking temperatures. Plants expressing a heat-stable NB-LRR polypeptide have an "increased level of resistance" as compared to a control plant at the "masking temperature" of the control plant, and are taken as being useful in the invention. Plants expressing a heat-stable NB-LRR polypeptide confer a heat-stable defense response to a plant pathogen, which is monitored and assessed according to standard methods known in the art and described herein. By "increased level of resistance" is meant a level of resistance to a disease-causing pathogen in a non-naturally occurring plant (or cell or seed thereof) which is greater than the level of resistance in a control plant (for example, a non-transgenic plant or wild-type or a transgenic plant or a wild-type plant with a heat-labile NB-LRR polypeptide). In preferred embodiments, the level of resistance in a non-naturally occurring transgenic plant of the invention is at least 5% to 20% (and preferably 30% or 40%) greater than the resistance exhibited by a control plant. In other preferred embodiments, the level of resistance to a disease-causing pathogen is 50% greater, 60% greater, and more preferably even 75% or 90% greater than a control plant; with up to 100%0 or greater above the level of resistance as compared to a control plant being most preferred. For example, a disease resistance response may be measured at 23° C., 24° C., 25° C., 26° C., 27° C., 28° C., 29° C., 30° C., 31° C., 32° C., 33° C., 34° C., 35° C., or greater relative to the masking temperature of a control plant which does not express a heat-stable NB-LRR disease resistance polypeptide. The level of resistance is measured using conventional methods such as those described herein. For example, the level of resistance to a pathogen may be determined by comparing physical features and characteristics (for example, plant height and weight) or by comparing disease symptoms (for example, delayed lesion development, reduced lesion size, leaf wilting and curling, water-soaked spots, amount of pathogen growth, and discoloration of cells) of the non-naturally occurring plant (e.g., a transgenic plant).

In one example, transgenic tobacco plants were engineered to express a heat-stable defense response by modifying N to confer a heat-stable disease resistance. Tobacco plants transformed with N genes with Y646K or Y646KN648D modifications were generated. Plants were infected with tobacco mosaic virus at 30° C. for seven (7) days. After 7 days, plants were shifted to 22° C. and analyzed for the spread of TMV occurred at 30° C. Transgenic tobacco expressing N genes with Y646K or Y646KN648D were found to be resistant to TMV as compared to control tobacco plants expressing the wild-type N gene at 30° C.

The invention also involves rendering heat-labile NB-LRR resistance genes heat-stable. This generally involves (1) identification of a heat-labile NB-LRR type of R gene, (2) Alignment of the protein sequence of Rs to those of SNC1 and N to identify LRR domain with identity to the heat-stability domain of SNC1; (3) Introduction of cognate mutations of snc1-3 into the Rs gene by site-directed mutagenesis; and (4) Assaying for temperature sensitivity.

1) Identification of the NB-LRR type of R gene responsible for resistance to a particular pathogen.

For heat-labile disease resistance, an R gene (referred to here as Rs) responsible for this resistance is identified. This is accomplished in a number of ways known in the art, for example, by map-based cloning exploring natural variations among different accessions of a plant species. Additional Rs genes are available in the art (See FIGS. 8 and 9). Rs genes may also be identified in databases (See FIGS. 8 and 9). Cloning and isolation of Rs is accomplished using standard methods known in the art.

2) Align the protein sequence of Rs to those of SNC1 and N and identify the corresponding residue of E640 of SNC1.

Most sequence analysis programs have a function for protein sequence alignment and can all be used for this purpose. For instance, NCBI has 'Blast 2' for aligning two sequences and Vector NTI has an alignment function for two or more sequences. NB-LRR proteins have CC or TIR domains at the N-terminus, ARC-linker domains in the middle, and LRR domains at the C-terminus. The ARC-linker and LRR domains usually have high sequence similarities among different R proteins and are aligned easily.

3) Introduction of cognate mutations of snc1-3 into the Rs gene by site-directed mutagenesis.

The corresponding region of SNC1 640ELD in the Rs protein is altered into KLD. This is achieved by commercially available site-directed mutagenesis kits available from a number of companies. For instance, 'Quick-change' from Invitrogen uses a complementary pair of primers with desired mutations a polymerase-chair reaction (PCR) to replace the wild-type sequences. The mutated Rs genes are sequenced to confirm that the desired mutations but not others are indeed introduced into the Rs protein.

4) Test the temperature sensitivity of the mutant Rs gene.

For those Rs genes where a transient assay for their activities are available (as for N and SNC1), the assay can be used to determine whether the mutant Rs gene confers disease resistance at a high temperature. For those Rs genes without a transient assay, procedures in step 6) are used. Such an assay involves co-infiltrating the pathogen elicitor gene and the plant Rs gene into *Nicotiana benthamiana* through *agrobacterium* and monitoring hypersensitive responses (HR) at different temperatures. If the mutant Rs gene induces HR at high temperature while the wild-type Rs does not, the mutant gene indeed harbors the heat-stable property. If no such activity is achieved, a screen for such a mutation is carried out as described below.

5) Isolate heat-stable mutations in the Rs gene Random-mutagenesis, for example, is also used to create a mutant library of the Rs gene. This is achieved according to standard techniques, for example, through error-prone PCR or error-prone replication using XI1-red cells. The DNA fragment coding for the linker and the LRR domains is subject to such mutagenesis so that every fragment will have 0.1-0.5% of the nucleotides altered. These mutant fragments are ligated with the rest of the Rs gene to reconstitute the full-length Rs genes. Other regions of an Rs gene may be mutagenized these include the CC or TIR domains at the N-terminus and ARC-linker domain. Any region of an Rs gene, in general, may be mutagenized to generate a library of mutants useful for analysis. A library consisting of these mutated Rs genes is then screened to identify mutants that have HR causing activity at high temperatures described in step 4 above according to standard methods.

6) If a transient assay for Rs gene activity is not available, the mutant Rs gene or the library of mutant Rs gene is transformed into disease susceptible plants and transgenic plants are assayed for disease resistance at elevated temperature. Those with heat-stable resistance are identified and selected according to the methods described herein.

The invention also features the following:

1) Breed Plants with Heat-Stable Resistance

Variations in a plant species (either wild varieties or cultivars) provide resources for R gene variations. NB-LRR genes are the most rapidly evolved compared to other genes in *Arabidopsis* (37) and this is likely true in other plant species. It is possible that one particular variety has already evolved to harbor heat-stable disease resistance by evolving a mutation in the Rs gene. The invention accordingly provides a quick screen for such an R variant to assist plant breeding.

PCR is then used to amplify the linker and LRR regions of the Rs gene from different plant varieties. Rs genes with positively charged residues (K, R, or H) at the position corresponding to 640E in SNC1 are good candidate for variant conferring heat-stable resistance. These varieties can be tested directly for disease resistance at high temperatures.

Once the heat-stable resistance conferred by an Rs variant is found, this Rs variant are introduced into crops by crossing the two varieties and isolating those with most of the elite traits together with the Rs variant in the F2 population with marker assisted selection.

Other examples of engineering a heat-stable defense response in crop plants include the following. To provide a heat-stable defense response in barley to combat powdery mildew caused by *Blumeria graminis*, R genes such as Mla1 and Mla6 are modified to express polypeptides (as compared to wild type R polypeptides) having Y613K G615D and V636K, respectively. In maize, R genes such as Rp1-D and Rp3 are respectively modified compared to wild type R polypeptides as follows: A676K E678D and A613K H615D to engineer a resistance polypeptide that combats leaf rust caused by *Puccinia sorghi*. Rice plants expressing a modified NB-LRR polypeptide (Xa1: E1086K E1088D) are useful for providing resistance to bacterial blight caused by *Xanthamonas oryzae* in a heat-stable defense response. Modification of the rice resistance gene Pi-b to express a NB-LRR polypeptide having Y1130K S1132D compared to wild type provides resistance to rice blast caused by *Magnaporthe grisea*. Leaf rust in wheat caused by *Puccinia triticina* may be combated in a heat-stable defense response by modification of the Lr21 protein as follows: M967K N969D. Powdery mildew in wheat caused by caused by *Blumeria graminis* is addressed by expression of a Pm3 polypeptide mutated as follows: V628K. *Phytophthora infestans* is a fungal pathogen that causes late blight in potato. Modification of a potato R gene in a transgenic potato, such as R1 (Q1203K) is useful for providing resistance to late blight in potato. In another example, transgenic tomato plants expressing Cf-2 (F243K F245D) are useful for providing resistance to leaf mould caused by *Cladosporium fulvum*. FIG. 11 summarizes the aforementioned modifications to wild type polypeptides to confer resistance in a variety of plants to various pathogens. FIG. 11 also shows alignment of R genes with SNC1.

Although the invention has been described in detail for the purpose of illustration, it is understood that such detail is solely for that purpose, and variations can be made therein by those skilled in the art without departing from the spirit and scope of the invention which is defined by the claims.

OTHER EMBODIMENTS

The invention provides methods of identifying, isolating, and using a nucleic acid molecule which encodes a NB-LRR disease resistant polypeptide which includes a heat-stable subdomain of the LRR.

A polypeptide that includes (a) a nucleotide binding (NB) domain and (b) a leucine rich repeat (LRR) domain, wherein the LRR domain includes a sub-domain that confers a heat-stable defense response to a plant pathogen includes variant polypeptides derived from a particular NB-LRR polypeptide by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the NB-LRR polypeptide. Such variants may result from, for example, from human manipulation. Methods for such manipulations are generally known in the art. For example, amino acid sequence variants of the polypeptides can be prepared by mutations in the DNA. Methods for mutagenesis and nucleotide sequence alterations are well known in the art. Guidance as to appropriate amino acid substitutions that do not affect biological activity of the protein of interest may be found in the art. Conservative substitutions, such as exchanging one amino acid with another having similar properties, are preferred.

Thus, the NB-LRR polypeptide genes and nucleotide sequences of the invention include both the naturally occurring sequences as well as mutant forms. Likewise, the NB-LRR polypeptides encompass both naturally occurring proteins as well as variations and modified forms thereof. Such variants will continue to possess the desired activity. The deletions, insertions, and substitutions of the NB-LRR polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays such as those described herein.

The nucleic acid molecules are optimized for enhanced expression in plants. In this manner, the genes or gene fragments can be synthesized utilizing plant-preferred codons according to methods well known in the art. It is recognized that all or any part of the gene sequence may be optimized or synthetic. That is, synthetic or partially optimized sequences may also be used. Variant nucleotide sequences and proteins also encompass sequences and protein derived from a mutagenic and recombinant procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art.

By "variants" is intended substantially similar sequences. For nucleotide sequences, variants include those sequences that, because of the degeneracy of the genetic code, encode the identical amino acid sequence of the reference protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the reference protein, as well as those that encode a polypeptide having amino acid substitutions. Generally, nucleotide sequence variants of the invention will have at least 40%, 50%, 60%, preferably 70%, more preferably 80%, even more preferably 90%, most preferably 99%, and single unit percentage identity to the native nucleotide sequence based on these classes. For example, 40%, 41%, 42% and the like, up to at least the 90% class. Variants may also include a full length gene corresponding to an identified gene fragment.

Nucleic acid molecules which are substantially identical to any of the nucleic acid molecules described herein which encode NB-LRR polypeptides having a heat-stable LRR subdomain are included within the scope of the invention (for example, a SNC1-3, SNC1 E640R, N Y646K, or N Y646K N648D polypeptide or any of the polypeptides described in FIG. 10).

By "substantially identical" is meant a polypeptide or nucleic acid exhibiting at least 40-50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. Generally, nucleotide sequences will again have at least 40%, 50%, 60%, preferably 70%, more preferably 80%, even more preferably 90%, most preferably 99%, and single unit percentage identity to the NB-LRR nucleotide sequence (or polypeptide) based on these classes. For example, 20%, 25%, 30%, 35%, 40%, 41%, 42% and the like, up to at least the 90% class.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Plant cells useful in the invention as sources of nucleic acid molecules encoding heat-stable NB-LRR polypeptides as well as recipients for transformation using isolated nucleic acids molecules include preferably those with an agronomic, horticultural, ornamental, economic, or commercial value, and more preferably is include, without limitation, *Acacia*, alfalfa, apple, aneth, apple, apricot, artichoke, arugula, *asparagus*, avocado, balsam poplar, banana, barley, beans, beet, black cottonwood, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, *eucalyptus*, fennel, figs, flax, French bean, garlic, gourd, grape, grapefruit, honey dew, Indian rice, Japanese rice, jicama, kiwifruit, lettuce, leeks, lemon, lime, Loblolly pine, linseed, mango, maize, melon, mushroom, nectarine, nut, oat, oil palm, oil seed rape, okra, olive, onion, orange, oriental melon, palm, *papaya*, parsley, parsnip, pea, peach, peanut, pear, pepper, persimmon, pine, pineapple, plantain, plum, pomegranate, poplar, potato, pumpkin, quince, *radiata* pine, radicchio, radish, rapeseed, raspberry, rice, rye, *sorghum*, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini cell.

REFERENCES

1. Jones, J. D. & Dangl, J. L. The plant immune system. Nature 444, 323-9 (2006).
2. Chisholm, S. T., Coaker, G., Day, B. & Staskawicz, B. J. Host-microbe interactions: shaping the evolution of the plant immune response. Cell 124, 803-14 (2006).
3. Samuel, G. Some experiments on inoculating methods with plant viruses, and on local lesions. Ann. Appl. Biol. 18, 494-507 (1931).
4. Dietrich, R. A. et al. *Arabidopsis* mutants simulating disease resistance response. Cell 77, 565-577 (1994).
5. Yoshioka, K. et al. Environmentally sensitive, SA-dependent defense responses in the cpr22 mutant of *Arabidopsis*. Plant J 26, 447-59 (2001).
6. Hwang, C. F., Bhakta, A. V., Truesdell, G. M., Pudlo, W. M. & Williamson, V. M. Evidence for a role of the N terminus and leucine-rich repeat region of the Mi gene product in regulation of localized cell death. Plant Cell 12, 1319-29. (2000).
7. Yang, S. & Hua, J. A haplotype-specific Resistance gene regulated by BONZAI1 mediates temperature-dependent growth control in *Arabidopsis*. Plant Cell 16, 1060-71 (2004).
8. Dangl, J. L. & Jones, J. D. Plant pathogens and integrated defence responses to infection. Nature 411, 826-833 (2001).
9. Martin, G., Bogdanove, A. & sessa, G. Understanding the functions of plant disease resistance proteins. Annu Rev Plant Biol 54, 23-61 (2003).
10. Zhang, Y., Goritschnig, S., Dong, X. & Li, X. A gain-of-function mutation in a plant disease resistance gene leads 11. Whitham, S. et al. The product of the tobacco mosaic virus resistance gene N: similarity to toll and the interleukin-1 receptor. Cell 78, 1101-15. (1994).
12. Uknes, S. et al. Acquired resistance in *Arabidopsis*. Plant Cell 4, 645-56 (1992).
13. Lawton, K. et al. Systemic acquired resistance in *Arabidopsis* requires salicylic acid but not ethylene. Mol Plant Microbe Interact 8, 863-70 (1995).
14. Jirage, D. et al. *Arabidopsis thaliana* PAD4 encodes a lipase-like gene that is important for salicylic acid signaling. Proc Natl Acad Sci USA 96, 13583-8. (1999).
15. Li, Y., Yang, S., Yang, H. & Hua, J. The TIR-NB-LRR gene SNC1 is regulated at the transcript level by multiple factors. Mol Plant Microbe Interact 20, 1449-56 (2007).
16. Wen, W., Meinkoth, J. L., Tsien, R. Y. & Taylor, S. S. Identification of a signal for rapid export of proteins from the nucleus. Cell 82, 463-73 (1995).
17. Shen, Q. H. et al. Nuclear activity of MLA immune receptors links isolate-specific and basal disease-resistance responses. Science 315, 1098-103 (2007).
18. Burch-Smith, T. M. et al. A Novel Role for the TIR Domain in Association with Pathogen-Derived Elicitors. PLoS Biol 5, e68 (2007).
19. Merkle, T. Nucleo-cytoplasmic partitioning of proteins in plants: implications for the regulation of environmental and developmental signalling. Curr Genet 44, 231-60 (2003).
20. Xu, X. M. & Meier, 1. The nuclear pore comes to the fore. Trends Plant Sci 13, 20-7 (2008).
21. Zhang, Y. & Li, X. A putative nucleoporin 96 Is required for both basal defense and constitutive resistance responses mediated by suppressor of npr1-1, constitutive 1. Plant Cell 17, 1306-16 (2005).
22. Palma, K., Zhang, Y. & Li, X. An importin alpha homolog, MOS6, plays an important role in plant innate immunity. Curr Biol 15, 1129-35 (2005).
23. Lange, A. et al. Classical nuclear localization signals: definition, function, and interaction with importin alpha. J Biol Chem 282, 5101-5 (2007).
24. Rathjen, J. P. & Moffett, P. Early signal transduction events in specific plant disease resistance. Curr Opin Plant Biol 6, 300-6 (2003).
25. Takken, F. L., Albrecht, M. & Tameling, W. I. Resistance proteins: molecular switches of plant defence. Curr Opin Plant Biol 9, 383-90 (2006).
26. Lukowitz, W., Gillmor, C. S. & Scheible, W. R. Positional cloning in *Arabidopsis*. Why it feels good to have a genome initiative working for you. Plant Physiol 123, 795-805 (2000).
27. Yang, H., Li, Y. & Hua, J. The C2 domain protein BAP1 negatively regulates defense responses in *Arabidopsis*. Plant J 48, 238-48 (2006).
28. Yang, H., Yang, S., Li, Y. & Hua, J. The *Arabidopsis* BAP1 and BAP2 genes are general inhibitors of programmed cell death. Plant Physiol 145, 135-46 (2007).
29. Tzfira, T. et al. pSAT vectors: a modular series of plasmids for autofluorescent protein tagging and expression of multiple genes in plants. Plant Mol Biol 57, 503-16 (2005).
30. Rairdan, G. J. & Moffett, P. Distinct domains in the ARC region of the potato resistance protein Rx mediate LRR binding and inhibition of activation. Plant Cell 18, 2082-93 (2006).
31. T. Nurnberger, F. Brunner, B. Kemmerling, L. Piater, Immunol Rev 198, 249 (April, 2004)
32. H. H. Flor, Annu. Rev. Phytopathol. 9, 275 (1971)
33. K. E. Hammond-Kosack, J. D. Jones, Plant Cell 8, 1773 (1996).
34. V. Dropkin, Phytopathology 59, 1632 (1969).
35. N. Someya, K. Niinuma, M. Kimura, 1. Yamaguchi, H. Hamamoto, Arch Virol 149, 2105 (2004)
36. S. Xiao, P. Charoenwattana, L. Holcombe, J. G. Turner, Mol Plant Microbe Interact 16, 289 (2003)
37. R. M. Clark et al. Science 317, 338 (2007)

What is claimed is:

1. A method of conferring resistance to a pathogen in a plant or plant component, the method comprising the steps of:
   (a) transforming a plant cell with a nucleic acid molecule operably linked to a heterologous promoter that encodes a polypeptide comprising:
   (i) a nucleotide binding (NB) domain; and
   (ii) a leucine rich repeat (LRR) domain having EKLD (SEQ ID NO: 3), ERLD (SEQ ID NO: 4), EKVN (SEQ ID NO: 6), EYVD (SEQ ID NO: 7), EKVD (SEQ ID NO: 8), ELXLD (SEQ ID NO: 9), or ELXLVX (SEQ ID NO: 10) sequences, wherein said polypeptide confers a heat-stable defense response to a plant pathogen, wherein said heat-stable defense response is at least 2° C. higher than the temperature at which the plant or plant component fails to meet the defense response in the absence of the polypeptide; and
   (b) regenerating a plant or plant component from said transformed plant cell, wherein said plant exhibits resistance to said pathogen.

2. The method of claim 1, wherein said nucleic acid molecule is operably linked to a promoter that drives expression in a plant cell.

3. The method of claim 1 wherein said plant or plant component is a monocot or a dicot.

4. The method of claim 1, wherein said pathogen is a bacterial, an insect, a nematode, a fungal, or a viral pathogen.

5. A plant or plant component comprising a heterologous genetically-modified polypeptide comprising:
   (a) a nucleotide binding (NB) domain; and
   (b) a leucine rich repeat (LRR) domain having an EKLD (SEQ ID NO: 3), ERLD (SEQ ID NO: 4), EKVN (SEQ ID NO: 6), EYVD (SEQ ID NO: 7), EKVD (SEQ ID NO: 8), ELXLD (SEQ ID NO: 9), or ELXLVX (SEQ ID NO: 10) sequence, wherein said polypeptide confers a heat-stable defense response to a plant pathogen, wherein said heat-stable defense response is at least 2° C. higher than the temperature at which the plant or plant component fails to meet the defense response in the absence of the polypeptide.

6. The plant or plant component of claim 5, wherein the sequence comprises EKLD (SEQ ID NO: 3).

7. The plant or plant component of claim 5, wherein the sequence comprises ERLD (SEQ ID NO: 4).

8. The plant or plant component of claim 5, wherein the sequence comprises EKVN (SEQ ID NO: 6).

9. The plant or plant component of claim 5, wherein the sequence comprises EYVD (SEQ ID NO: 7).

10. The plant or plant component of claim 5, wherein the sequence comprises EKVD (SEQ ID NO: 8).

11. The plant or plant component of claim 5, wherein the sequence comprises ELXLD (SEQ ID NO: 9).

12. The plant or plant component of claim 5, wherein the sequence comprises ELXLVX (SEQ ID NO: 10).

13. The plant or plant component of claim 5, wherein said plant or plant component is a monocot or a dicot.

14. The plant or plant component of claim 5, wherein said plant component is a somatic embryo, a leaf, a stem, a root, a flower, a fruit, a scion, or a rootstock.

15. The plant or plant component of claim 5, wherein said plant component is a seed.

16. The plant or plant component of claim 5, wherein said polypeptide is expressed under the control of a plant promoter or a cauliflower mosaic virus promoter in said plant or plant component.

17. The method of claim 1, wherein the sequence comprises EKLD (SEQ ID NO: 3).

18. The method of claim 1, wherein the sequence comprises ERLD (SEQ ID NO: 4).

19. The method of claim 1, wherein the sequence comprises EKVN (SEQ ID NO: 6).

20. The method of claim 1, wherein the sequence comprises EYVD (SEQ ID NO: 7).

21. The method of claim 1, wherein the sequence comprises EKVD (SEQ ID NO: 8).

22. The method of claim 1, wherein the sequence comprises ELXLD (SEQ ID NO: 9).

23. The method of claim 1, wherein the sequence comprises ELXLVX (SEQ ID NO: 10).

24. The method of claim 1, wherein said plant or plant component is a monocot or a dicot.

25. The method of claim 1, wherein said plant component is a somatic embryo, a leaf, a stem, a root, a flower, a fruit, a scion, or a rootstock.

26. The method of claim 1, wherein said plant component is a seed.

27. The method of claim 1, wherein said polypeptide is expressed under the control of a plant promoter or a cauliflower mosaic virus promoter in said plant or plant component.

* * * * *